(12) United States Patent
Shimaoka et al.

(10) Patent No.: US 9,335,254 B2
(45) Date of Patent: May 10, 2016

(54) PAPER SHEET RECOGNITION APPARATUS, LIGHT GUIDE AND LIGHT GUIDE CASING FOR USE IN SPECTROMETRIC MEASUREMENT OF PAPER SHEET

(75) Inventors: Fumiaki Shimaoka, Hyogo (JP); Takeshi Sato, Hyogo (JP); Hiroshi Konishi, Hyogo (JP); Takashi Inoue, Hyogo (JP)

(73) Assignee: GLORY LTD., Himeji-shi, Hyogo (JP)

( * ) Notice: Subject to any disclaimer, the term of this patent is extended or adjusted under 35 U.S.C. 154(b) by 153 days.

(21) Appl. No.: 14/240,437

(22) PCT Filed: Aug. 27, 2012

(86) PCT No.: PCT/JP2012/071553
§ 371 (c)(1),
(2), (4) Date: Feb. 24, 2014

(87) PCT Pub. No.: WO2013/027848
PCT Pub. Date: Feb. 28, 2013

(65) Prior Publication Data
US 2014/0218734 A1  Aug. 7, 2014

(30) Foreign Application Priority Data
Aug. 25, 2011  (JP) .................................. 2011-183602

(51) Int. Cl.
*G06K 9/74* (2006.01)
*G01N 21/25* (2006.01)
(Continued)

(52) U.S. Cl.
CPC ................. *G01N 21/25* (2013.01); *G01N 21/21* (2013.01); *G07D 7/121* (2013.01); *G07D 7/122* (2013.01)

(58) Field of Classification Search
CPC ........................................................ G06K 9/74
USPC ............................................................ 356/71
See application file for complete search history.

(56) References Cited

U.S. PATENT DOCUMENTS 4,146,792 A    3/1979  Stenzel et al.
4,319,137 A *  3/1982  Nakamura ............... G07D 7/20
                                                          250/556

(Continued)

FOREIGN PATENT DOCUMENTS

DE    27 13 396 A1    9/1978
EP    1 239 423 A2    9/2002

(Continued)

OTHER PUBLICATIONS

Japanese Office Action (Application No. 2013-530078) (3 pages—dated Nov. 25, 2014).

(Continued)

*Primary Examiner* — Roy M Punnoose
(74) *Attorney, Agent, or Firm* — Renner, Kenner, Greive, Bobak, Taylor & Weber

(57) ABSTRACT

A paper sheet recognition apparatus that recognizes a paper sheet based on optical characteristics of the paper sheet is proposed. The paper sheet recognition apparatus includes at least one light source that emits a light toward the paper sheet; a light-guiding member that receives any of reflected lights reflected from plural regions on the paper sheet and transmitted lights that have passed through plural regions on the paper sheet because of emission of the light on the paper sheet from the light source, condenses the received lights, and outputs the condensed light from a light outputting section; an optical processing unit that generates spectral distribution from the condensed light output from the light outputting section of the light-guiding member; and a recognition processing unit that recognizes the paper sheet based on a feature of the spectral distribution generated by the optical processing unit.

17 Claims, 18 Drawing Sheets

(51) Int. Cl.
  *G07D 7/12*   (2016.01)
  *G01N 21/21*  (2006.01)

(56) References Cited

U.S. PATENT DOCUMENTS

| | | | | |
|---|---|---|---|---|
| 4,598,205 | A * | 7/1986 | Kaule | B41M 3/144 |
| | | | | 250/458.1 |
| 4,922,109 | A | 5/1990 | Bercovitz et al. | |
| 5,304,813 | A * | 4/1994 | De Man | G07D 7/121 |
| | | | | 250/226 |
| 5,498,879 | A * | 3/1996 | De Man | G07D 7/121 |
| | | | | 250/226 |
| 5,640,246 | A * | 6/1997 | Castonguay | G01N 21/474 |
| | | | | 250/227.28 |
| 5,781,293 | A | 7/1998 | Padgett et al. | |
| 6,061,121 | A | 5/2000 | Holl et al. | |
| 6,707,548 | B2 * | 3/2004 | Kreimer | G01J 3/02 |
| | | | | 356/301 |
| 7,277,569 | B2 * | 10/2007 | Bruce | B82Y 5/00 |
| | | | | 382/128 |
| 7,545,498 | B2 * | 6/2009 | Krivacic | G01N 21/6428 |
| | | | | 250/461.2 |
| 7,819,434 | B2 * | 10/2010 | Schwenk | B42D 25/29 |
| | | | | 283/57 |
| 8,536,516 | B2 * | 9/2013 | Ford | G01J 3/02 |
| | | | | 250/256 |
| 2002/0108891 | A1 | 8/2002 | Dunlop et al. | |
| 2004/0131241 | A1 * | 7/2004 | Curry | G01N 15/1468 |
| | | | | 382/133 |
| 2005/0040315 | A1 | 2/2005 | Jespersen et al. | |
| 2007/0187579 | A1 | 8/2007 | Wunderer et al. | |
| 2008/0273789 | A1 | 11/2008 | Bell et al. | |
| 2014/0204365 | A1 * | 7/2014 | Frankenberger | G07D 7/128 |
| | | | | 356/71 |

FOREIGN PATENT DOCUMENTS

| | | |
|---|---|---|
| JP | 10-143705 | 5/1998 |
| WO | WO 2009/110064 A1 | 9/2009 |
| WO | WO 2009/157049 A1 | 12/2009 |

OTHER PUBLICATIONS

Russian Office Action with English Translation (Application No. 2014111176—PCT/JP2012/071553) (7 pages—dated Oct. 7, 2015).
European Search Report (Application No. 12826278.9—PCT/JP2012/071553) (9 pages—dated May 2, 2015).

* cited by examiner

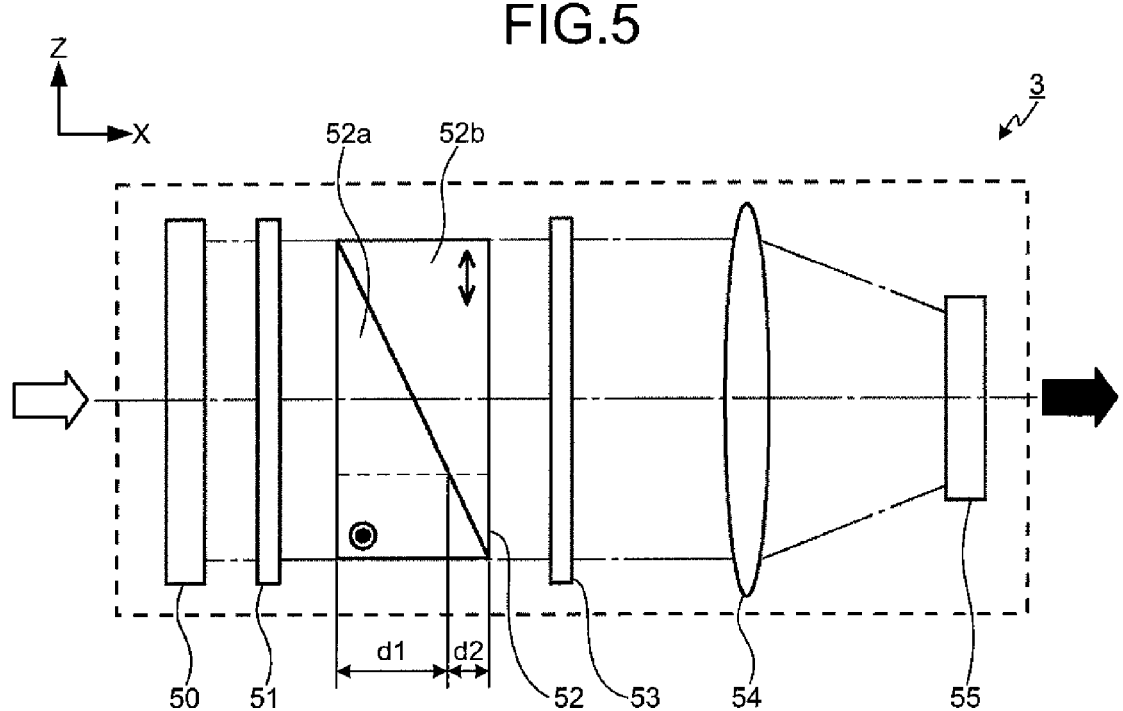

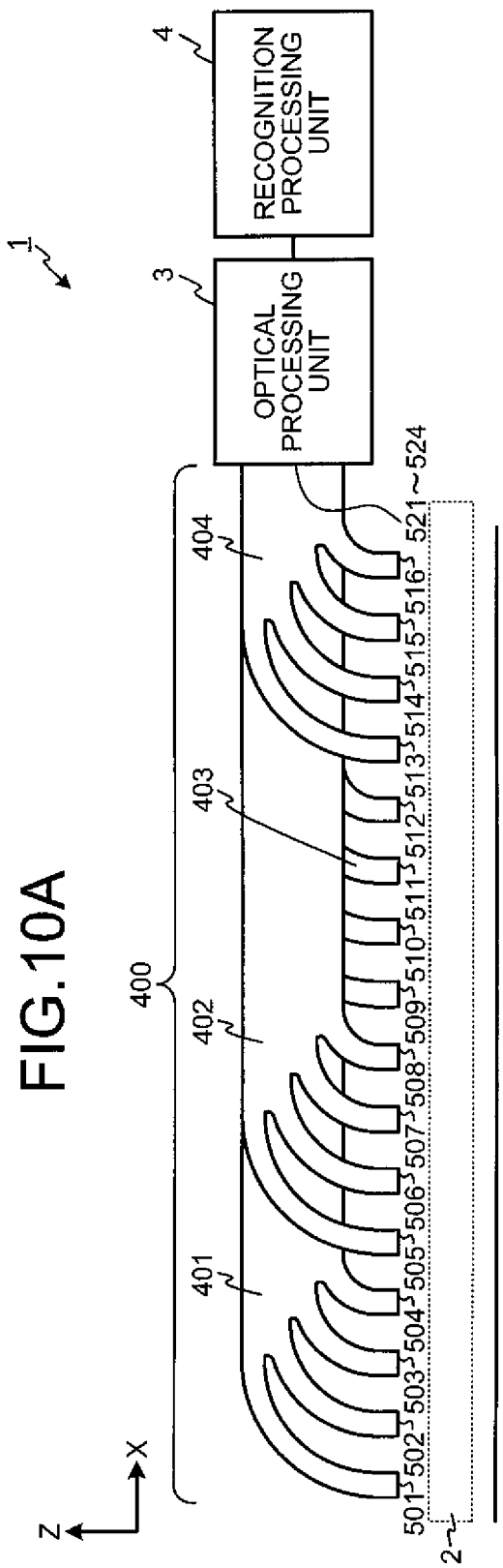
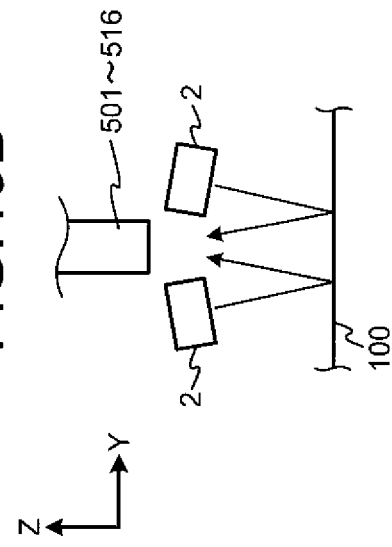

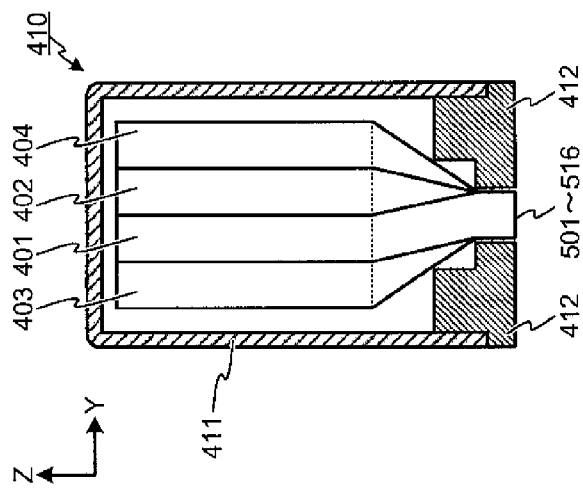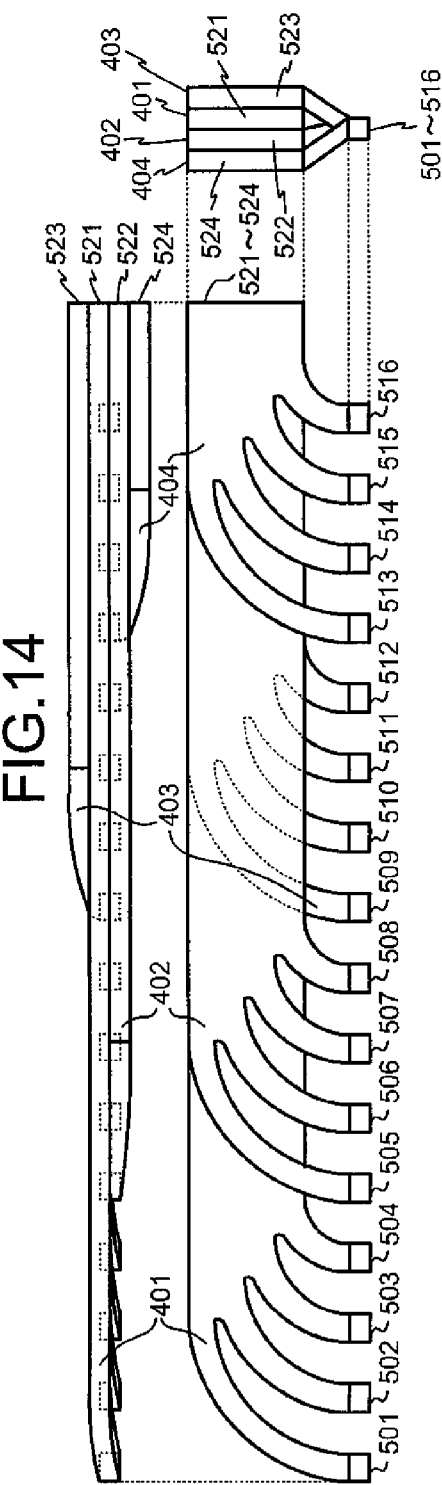

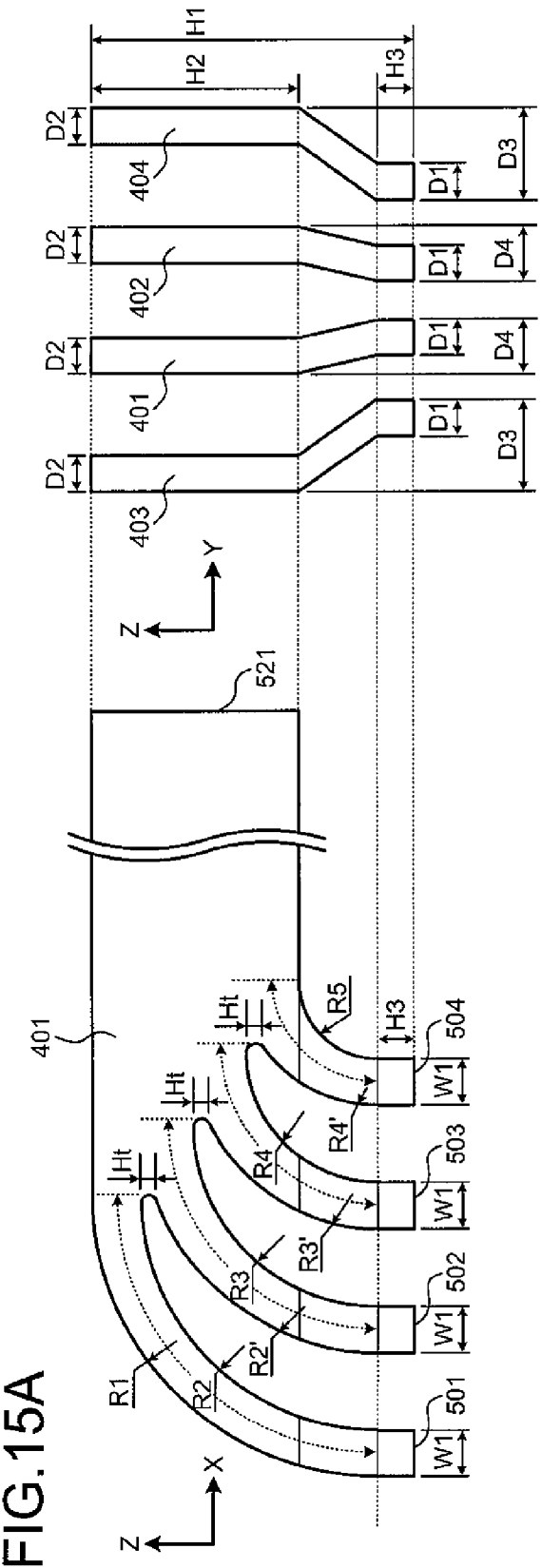
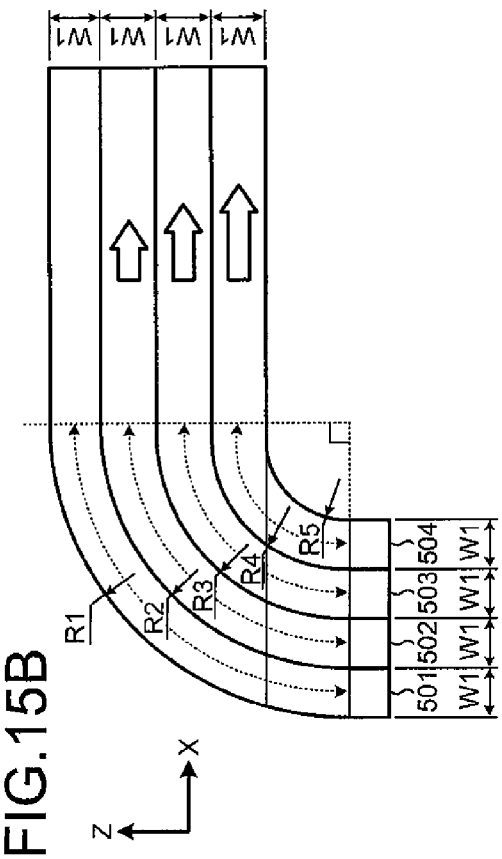
FIG.15A
FIG.15B

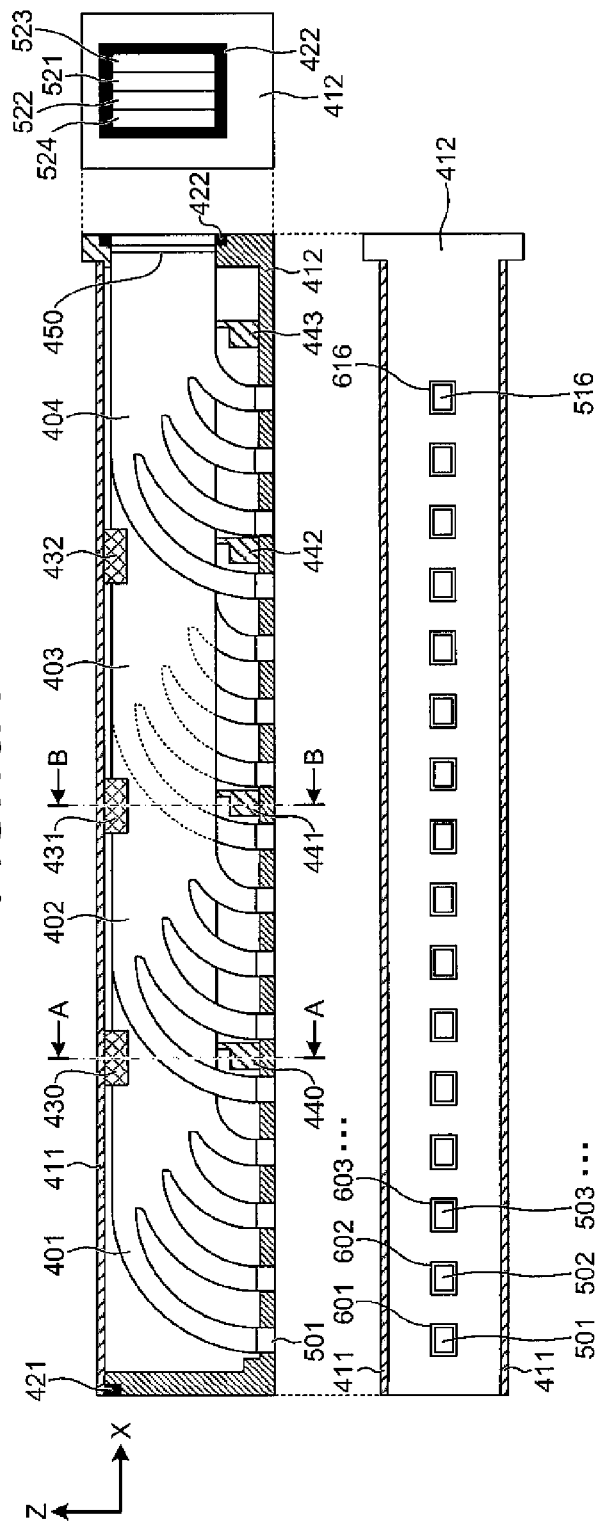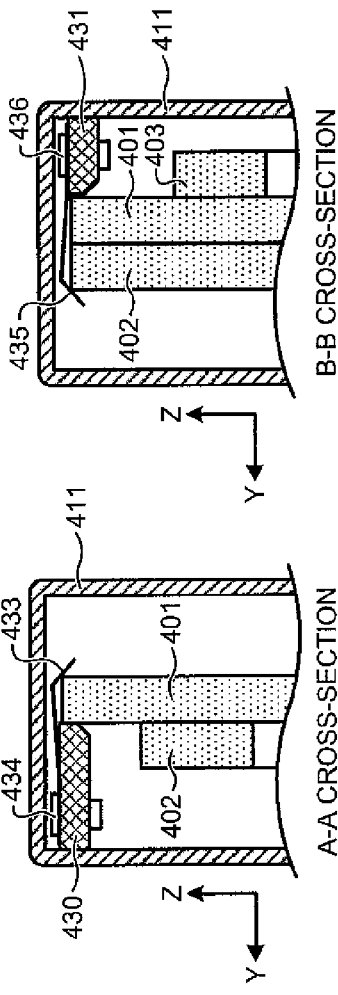

PAPER SHEET RECOGNITION APPARATUS, LIGHT GUIDE AND LIGHT GUIDE CASING FOR USE IN SPECTROMETRIC MEASUREMENT OF PAPER SHEET

TECHNICAL FIELD

The present invention relates to a paper sheet recognition apparatus that can recognize a paper sheet, alight guide that can be used in the paper sheet recognition apparatus when performing spectrometric measurement of the paper sheet to obtain optical characteristics of the paper sheet, and a light guide casing that can house the light guide.

BACKGROUND ART

A technology for recognizing denomination, authenticity, and fitness of a banknote by analyzing the optical characteristics of the banknote, obtained by emitting a light toward the banknote and measuring a reflected light reflected from the surface of the banknote or a transmitted light transmitted through the banknote, is known in the art. For example, Patent Document 1 discloses a banknote recognition apparatus that measures the optical characteristics of a banknote by using plural types of light sources aligned in a line, including ultraviolet light sources or infrared light sources, and sensors arranged corresponding to these light sources. On the other hand, Patent Document 2 discloses a device that recognizes a banknote by generating two reflected lights of different wavelength bands by filtering an ultraviolet light reflected from the surface of the banknote, measuring these reflected lights at respective sensors, and subjecting the measurement result to spectral analysis.

If a banknote has optical characteristics for an ultraviolet light or an infrared light, then it is possible to recognize this banknote by emitting the ultraviolet light or the infrared light toward the banknote and analyzing intensities of a reflected light or a transmitted light obtained from the banknote. On the other hand, if there are plural types of banknotes as the processing targets, these banknotes can be recognized by analyzing their spectral distributions if a spectral distribution of a reflected light or a transmitted light obtained from these banknotes when these banknotes are being irradiated with an ultraviolet light or an infrared light is different per denomination. Because such optical characteristics are measured in each of a plurality of partial regions on the banknote, plural light sources, each of which can emit an inspection light of a specific wavelength toward each of the partial regions, are arranged, and plural sensors are arranged corresponding to the plural light sources. Recognition of the banknote is performed by using the data obtained by these sensors.

CONVENTIONAL ART DOCUMENTS

Patent Documents

[Patent Document 1] Japanese Patent 3152372
[Patent Document 2] Japanese Patent Application Laid-open No. 10-143705

DISCLOSURE OF INVENTION

Problems to be Solved by the Invention

The above conventional technology requires plural sensors corresponding to the plural inspection lights used as light sources. In addition, because the data collected by each of the sensors needs to be processed separately, the processing contents and the processing circuit become complicated. Accordingly, the conventional technology had problems that the device size was large and the manufacturing costs were high.

For example, when measuring the optical characteristics by using each of an infrared light and an ultraviolet light as inspection lights, a light source and a sensor corresponding to each of the light sources is required to be arranged for each inspection light, and the measurement result obtained by using each of the light sources needs to be processed separately. In addition, filters and the like may be required if the optical characteristics of a specific band are to be measured. As a result, there are problems that not only the device structure but also the processing contents become complicated.

One approach to take care of the above problems can be to use a light guide and guide the measurement target light to one sensor by using this light guide. It is desirable that such a light guide be compact, like a line sensor used in a banknote recognition apparatus to obtain an image of the entire surface of a banknote, as well as be able to effectively measure the optical characteristics of the entire surface of the banknote. However, it is difficult to realize such a light guide.

Furthermore, assuming that such a light guide is somehow realized, it is desirable that other components do not touch the light guide if the received light is to be effectively guided to the sensor. In addition, in order to use the light guide, a light guide casing that can house the light guide while satisfying all such limitations is required.

The present invention has been made in order to solve the drawbacks in the above conventional technology. It is an object of the present invention to provide a paper sheet recognition apparatus that can recognize the optical characteristics of a paper sheet speedily with a simple structure, a light guide for spectrometric measurement of a paper sheet that can be used in the paper sheet recognition apparatus to effectively measure optical characteristics of a large region on the paper sheet, and a light guide casing that can house the light guide while maintaining a high performance of the light guide casing.

Means to Solve the Problems

To solve the above problems and to achieve the above objects, a paper sheet recognition apparatus that recognizes a paper sheet based on optical characteristics of the paper sheet according to an aspect of the present invention includes at least one light source that emits a light toward the paper sheet; a light-guiding member that receives any of reflected lights and transmitted lights from plural regions on the paper sheet irradiated with the light from the light source, condenses the received lights, and outputs the condensed light from a light outputting section; an optical processing unit that generates spectral distribution from the condensed light output from the light outputting section of the light-guiding member; and a recognition processing unit that recognizes the paper sheet based on a feature of the spectral distribution generated by the optical processing unit.

In a paper sheet recognition apparatus according to another aspect of the present invention, in the above aspect, the recognition processing unit performs at least one of a denomination recognition and an authenticity recognition based on the feature of the spectral distribution.

A paper sheet recognition apparatus according to still another aspect of the present invention, in the above aspect, further includes a light source control unit that controls the light source, and the plural light sources are arranged corresponding to plural of regions on the paper sheet, and the light-guiding member receives any of the reflected lights or the transmitted lights from the regions irradiated with the light from the light sources under the control of the light source control unit.

In a paper sheet recognition apparatus according to still another aspect of the present invention, in the above aspect, the optical processing unit generates the interference fringes from a light output from a light output surface of the light-guiding member, and the recognition processing unit recognizes the paper sheet based on the interference fringes generated by the optical processing unit.

In a paper sheet recognition apparatus according to still another aspect of the present invention, in the above aspect, the optical processing unit includes a first polarization plate that receives the light output from the light outputting section of the light-guiding member and converts the received light to linear polarized light; a prism that receives the linear polarized light converted by the first polarization plate and outputs an abnormal light and a normal light having mutual phase difference depending on the receiving position of the linear polarized light; and a second polarization plate that receives the abnormal light and the normal light output from the prism and converts the abnormal light and the normal light to a linear polarized light, and the interference fringes are generated by the linear polarized light output from the second polarization plate.

In a paper sheet recognition apparatus according to still another aspect of the present invention, in the above aspect, the prism is a Wollaston prism that includes a wedged-shaped first birefringence material that has different refractive indexes for the abnormal light and the normal light, and a wedged-shaped second birefringence material that has a different crystal axis than that of the first birefringence material.

In a paper sheet recognition apparatus according to still another aspect of the present invention, in the above aspect, the first polarization plate and the second polarization plate convert the received lights to a linear polarized light wave that is inclined by 45 degrees to a vertical direction.

In a paper sheet recognition apparatus according to still another aspect of the present invention, in the above aspect, the recognition processing unit generates a frequency distribution by subjecting the interference fringes generated in the optical processing unit to Fourier conversion and recognizes the paper sheet based on features of the frequency distribution.

A light guide for spectrometric measurement of a paper sheet that can be used to perform spectrometric measurement on a surface of the paper sheet according to still another aspect of the present invention includes a plurality of light receiving sections each having a light receiving surface that faces toward the paper sheet to receive a light from the surface of the paper sheet; and a light outputting section that outputs the lights received from the light receiving sections in a direction that is different from a direction from which the lights were received, wherein the light receiving sections are arranged by adjusting their intervals and heights so that two adjacent light receiving sections are arranged away from each other and their measurement regions where lights can be measured effectively are either in contact with each other or with partially overlapped adjacent sections in an arrangement direction, and lights from a continuous region in the arrangement direction on the paper sheet can be received.

A light guide for spectrometric measurement of a paper sheet according to still another aspect of the present invention, in the above aspect, further includes a plurality of light-guiding plates arranged in an array in a direction of thickness, wherein the light receiving sections are formed by being separated in each of the light-guiding plates.

In a light guide for spectrometric measurement of a paper sheet according to still another aspect of the present invention, in the above aspect, the light-guiding plates have a bend portion that is bent in a direction of thickness at a portion that branches into light receiving sections respectively such that, when the light-guiding plates are arranged in the direction of thickness, all the light-guiding plates are aligned in a line.

In a light guide for spectrometric measurement of a paper sheet according to still another aspect of the present invention, in the above aspect, each of the light-guiding plates is arranged such that, bend angles of the light-guiding plates, in which a distance from the light outputting sections to the light receiving sections is longer, are smaller than bend angles of the light-guiding plates, in which a distance from the light outputting sections to the light receiving sections is shorter.

In a light guide for spectrometric measurement of a paper sheet according to still another aspect of the present invention, in the above aspect, each of the light-guiding plates has an arc-shaped portion, when viewed from a side thereof, having the uniform cross section from the base of the branch to the end in branch areas leading to the plural light receiving sections.

In a light guide for spectrometric measurement of a paper sheet according to still another aspect of the present invention, in the above aspect, in each of the light-guiding plates, an external radius of a first arc-shaped portion and an internal radius of an adjacent second arc-shaped portion at outer side are equal.

A light guide for spectrometric measurement of a paper sheet according to still another aspect of the present invention, in the above aspect, further includes a partition plate that blocks out a light and that is arranged between adjacent light receiving sections.

A light guide casing that houses the above light guide such that only the light receiving sections and the light outputting section are exposed to outside according to still another aspect of the present invention includes a base member that positions and supports each of light-guiding plates from below; and a cover member that positions and supports each of light-guiding plates from above, wherein the base member and the cover member make a contact with the light guide only at a corner portion of the light-guiding plate.

In a light guide casing according to still another aspect of the present invention, in the above aspect, the cover member includes an upper holding member having a main body and a plate spring fixed to the main body, and the upper holding member positions and fixes the light-guiding plates by pressing a side surface of the light-guiding plates to the main body by the plate spring.

In a light guide casing according to still another aspect of the present invention, in the above aspect, the base member includes a lower holding member that has a groove portion for positioning the light-guiding plate, wherein only both outer side portions of the lower holding member that are formed higher as compared to a central portion of the bottom surface contact with lower corners of the light guiding-plate at the bottom of the groove portion, and only lower portion of the lower holding member that are formed narrower as compared to an upper portion contact with the lower corners of the light-guiding plate at both outer sides of the groove portion.

Advantages of the Invention

According to the present invention, because plural regions of which optical characteristics can be measured and that can be used in for recognizing a paper sheet are set on the paper sheet, and the lights measured from those regions are condensed and used in the recognition process, there is no need to arrange plural sensors that individually process the light. Accordingly, the device structure can be prevented from becoming complicated while maintaining the accuracy in recognizing the paper sheet. Moreover, although the light received from the paper sheet is condensed and used, because this process is an optical process, the processing speed is high.

According to the present invention, plural regions of which optical characteristics can be measured and that can be used in a recognition process, such as a denomination recognition or a fitness detection, of a paper sheet are set on the paper sheet, the light to be measured from each of those regions is condensed, and the recognition process is performed based on the condensed light. Accordingly, depending on the regions set on the paper sheet, in one processing, for example, either of the denomination recognition or the fitness detection can be performed, or both the denomination recognition and the fitness detection can be performed.

According to the present invention, plural light receiving sections are arranged such that their measurement regions on the paper sheet abut each other. Accordingly, the optical characteristics can be measured in a continuous region in the arrangement direction of the light receiving sections.

According to the present invention, plural light receiving sections are arranged in each of a plurality of light-guiding plates. Accordingly, the optical characteristics can be measured more effectively than in a case where all the light receiving sections are arranged in a single light-guiding plate.

According to the present invention, plural light-guiding plates are arranged in their direction of thickness, and a portion of each of the light-guiding plates is bent in the direction of thickness to achieve arrangement of plural light receiving sections in a line. Accordingly, it is possible to scan the entire surface of the paper sheet and measure its optical characteristics.

According to the present invention, each of the light-guiding plates is arranged such that, bend angles of the light-guiding plates, in which a distance from the light receiving sections to a light outputting section is longer, are smaller than bend angles of the light-guiding plates, in which a distance from the light receiving sections to the light outputting section is shorter. Accordingly, unbalanced decay among the lights from the light-guiding plates can be prevented by maintaining a balance between the decay of the light due to the bends and the decay of the lights due to the distance between the light receiving sections and the light outputting section.

According to the present invention, because the light-guiding plate has an arc-shaped region in a side view in a region where each of the light-guiding plate is branched on the way from the light outputting section to the light receiving sections, the light received at the light receiving sections can be guided to the light outputting section while causing total reflection inside the light-guiding plate. Accordingly, the received light can be guided effectively to the light outputting section.

According to the present invention, each of the light-guiding plates that constitute the light guide and the light guide casing that houses the light-guiding plates do not touch in a region other than the corners of the light-guiding plates. Accordingly, a leakage of the light to the outside from the light-guiding plates can be suppressed to the minimal.

BRIEF DESCRIPTION OF DIAGRAMS

FIG. 5 is a schematic structural diagram of an optical processing unit according to the first embodiment.

FIGS. 10A and 10B are schematic structural diagrams of a banknote recognition apparatus according to a second embodiment.

FIG. 13 is a schematic cross-sectional diagram for explaining shape of a bend in each of light-guiding plates included in the light guide according to the second embodiment.

FIG. 14 is a schematic diagram for explaining a positional relationship among each of the light-guiding plates according to the second embodiment.

FIGS. 15A and 15B are schematic diagrams for explaining each shape of the light-guiding plates according to the second embodiment.

FIGS. 16A to 16C are schematic diagrams for explaining how the light guide according to the second embodiment is fixed inside a casing.

EMBODIMENTS OF THE INVENTION

Exemplary embodiments of a paper sheet recognition apparatus, a light guide that can be used in the paper sheet recognition apparatus when performing spectrometric measurement of the paper sheet to obtain optical characteristics of the paper sheet, and a light guide casing that can house the light guide according to the present invention are explained below while referring to the accompanying diagrams. In the following explanation, a banknote is taken as an example of a paper sheet.

First Embodiment

Figure 1A:
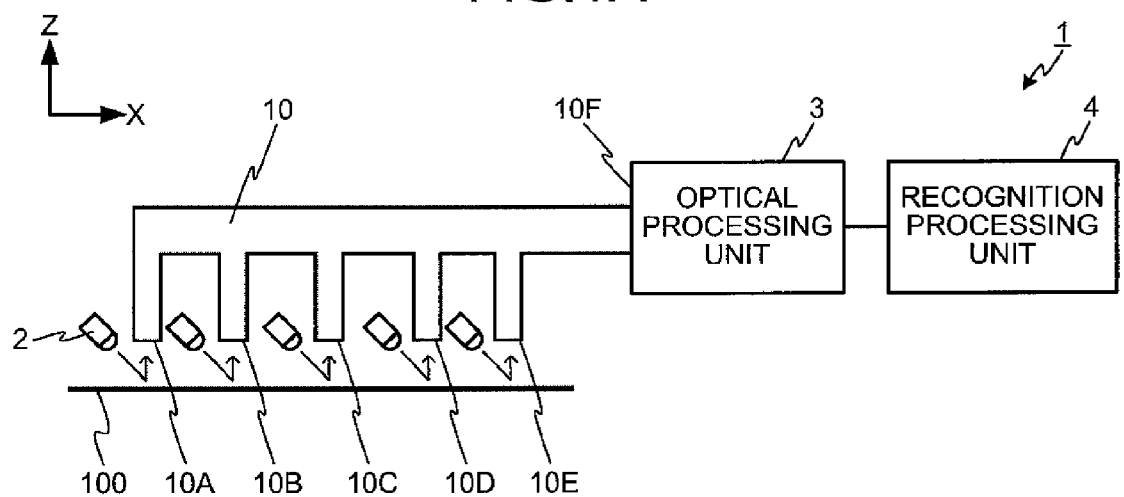
FIGS. 1A and 1B are schematic structural diagrams of a banknote recognition apparatus according to a first embodiment.
Figure 1B:
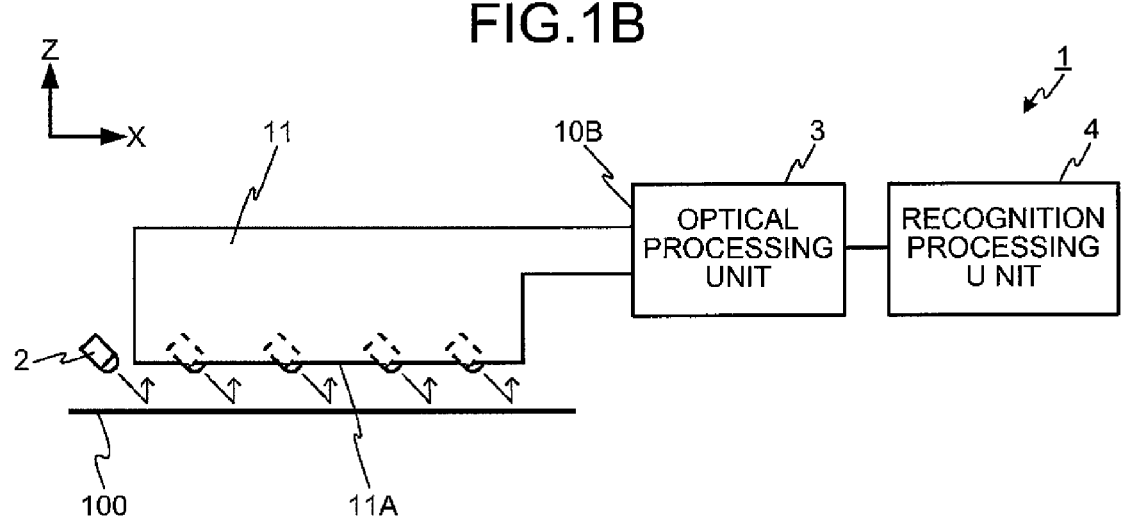

Outlines of a banknote recognition apparatus 1 are shown in FIGS. 1A and 1B. As shown in FIG. 1A, the banknote recognition apparatus 1 includes, for the purpose of recognizing a banknote 100, plural light sources 2 that respectively emit a light toward the banknote 100; a light guide 10 that receives reflected lights from the banknote 100, which was irradiated by the lights from the light sources 2, at respective light receiving sections, and outputs the received light from a light outputting section; an optical processing unit 3 that receives the light reflected from the banknote 100 via the light guide 10; and a recognition processing unit 4 that processes information obtained from the light processed at the optical processing unit 3.

FIG. 1B shows the banknote recognition apparatus 1 that includes a light guide 11 having a different configuration from the one shown in FIG. 1A. The basic configuration other than the light guide 11 is the same as that shown in FIG. 1A. The banknote recognition apparatus 1 shown in FIG. 1A or FIG. 1B has a structure in which the light guide 10 or the light guide 11 is firmly fixed to the optical processing unit 3. However, a structure is available in which the light guide 10 or the light guide 11 is detachable from the optical processing unit 3, and the light guide 10 or the light guide 11 is interchangeable to realize the structure shown in FIG. 1A or FIG. 1B.

Other than the functional units shown in FIGS. 1A and 1B, the banknote recognition apparatus 1 includes other units such as a transport unit that transports the banknote 100, a timing sensor that decides a start timing of a processing based on detection of arrival of the banknote 100, and communications interface that performs transmission/reception of data to/from other devices. Because these other units are the same as those in the conventional technology, an explanation thereof has been omitted herefrom. Moreover, explained below is the banknote recognition apparatus 1 that uses a reflected light reflected from the banknote 100. However, the structure is not limited to the one that uses the reflected light. For example, the banknote recognition apparatus 1 can be configured to use a transmitted light that is transmitted through the banknote 100, or can be configured to use both the reflected light and the transmitted light. Because the optical processing explained later is the same for any one of these configurations, this embodiment will be explained by using only the reflected light.

The light source 2 is, for example, an LED or a lamp, and emits a light toward the banknote 100 as a recognition target. As shown in FIG. 1A, for example, the light source 2 that includes one unit of a white LED corresponding to each of a plurality of light receiving sections 10A to 10E of the light guide 10 can be used. However, as long as the optical processing unit 3 receives sufficient amount of light through the light guide 10 or the light guide 11, the number and types of LEDs and the like included in the light sources 2 is not particularly limited. Light amount adjustment of the light sources 2, ON or OFF timing of the light sources 2 is controlled by the recognition processing unit 4 that functions as a light source control unit.

The light guide 10 or the light guide 11 is a light-guiding plate (light-guiding member) made of, for example, colorless and transparent resin material or glass material. The light guide 10 or the light guide 11 receive a light from one or more light receiving sections and outputs the received light from a predetermined light outputting section. The light guide 10 shown in FIG. 1A receives lights from five light receiving sections 10A to 10E arranged above (positive Z axis direction) the banknote 100. In contrast, in the light guide 11 shown in FIG. 1B that includes one light receiving section 11A arranged above the banknote 100, the entire surface facing the banknote 100 functions as a light receiving surface. FIGS. 1A and 1B schematically show the light guides 10 and 11, and the light guides 10 and 11 have structures that are concretely shown, for example, in FIGS. 2A and 2B.

Figure 2A:
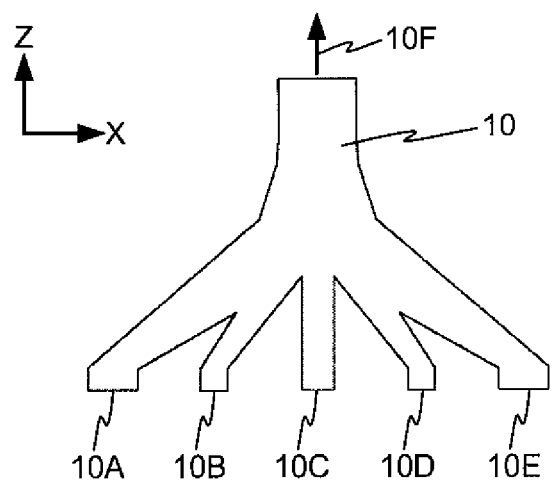
FIGS. 2A and 2B are structural diagrams of light guides that can be used in the banknote recognition apparatus according to the first embodiment.

The light guide 10 shown in FIG. 2A condenses the light received at each of the five light receiving sections 10A to 10E that are arranged in the banknote recognition apparatus 1 facing the banknote 100, and outputs the condensed light to the optical processing unit 3 via a single light outputting section 10F. The shape of the light guide 10 is optically designed such that the light received at each of the light receiving sections 10A to 10E is reflected internally and output from the light outputting section 10F. In addition, the shape of the light guide 10 is optically designed such that the light received at each of the light receiving sections 10A to 10E, which are aligned in the X axis direction, can be transmitted to the light outputting section 10F, which is arranged substantially at the center in the X axis direction, without undergoing a substantial change in its intensity.

Concretely, for example, as one goes farther from the light receiving section 10C that is arranged at substantially at the center in the X axis direction, a surface area of a light receiving surface is made larger. That is, the surface areas of the light receiving sections 10B and 10D are made larger than the same of the light receiving section 100, and the surface areas of the light receiving sections 10A and 10E are made larger than those of the light receiving sections 10B and 10D.

Adjustment of receiving light amount can be achieved by optical designing by taking into consideration the shape of the light guide, such as the shapes of the light receiving sections and the like, and the material and the like of the light guide. Alternatively, adjustment of the receiving light amount can be achieved by controlling the light sources 2. Concretely, assuming that the surface areas of the light receiving surfaces of the light receiving sections 10A to 10E of the light guide 10 shown in FIG. 2A are equal, then adjustment of receiving light amount can be achieved by controlling the light amount emitted from the light sources 2 provided corresponding to the light receiving sections 10A to 10E. In this manner, by controlling the light amount emitted from the light sources 2 based on the shape of the light guide 10 or an optical path length and the like from the light receiving sections 10A to 10E to the light outputting section 10F, the light amount reaching to the light outputting section 10F from the light receiving sections 10A to 10E can be controlled. Generally, the adjustment of the light amount is performed such that the light received at each of the light receiving sections 10A to 10E reach the light outputting section 10F at substantially the same intensity; however, it is possible to intentionally change the intensities. Concretely, the amount of the light to be emitted and the timing of emission of the light from each of the light sources 2 arranged corresponding to each of the light receiving sections 10A to 10E can be changed. For example, a stronger light can be emitted in one region on the banknote 100 and a weaker light can be emitted in a different region on the banknote 100. The control of the shape of the light guide 10 or each of the light sources 2 is performed appropriately such that the features of the banknote 100 become apparent in the later-explained spectroscopic analysis performed in order to recognize the banknote 100.

Figure 2B:
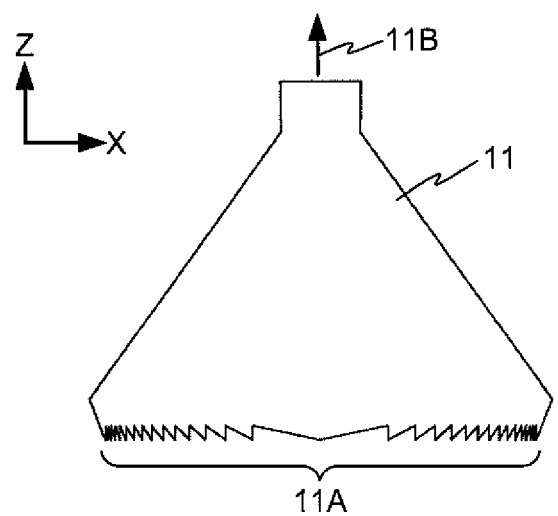

In the light guide 11 shown in FIG. 2B, the light received at the light receiving section 11A arranged facing the banknote 100 in the banknote recognition apparatus 1 is output to the optical processing unit 3 via a light outputting section 11B. The shape of the light guide 11 is determined based on optical designing such that the light received at the light receiving section 11A is output from the light outputting section 11B. A Fresnel lens is provided in the light receiving section 11A so that it can condense the light. Even the light guide 11 shown in FIG. 2B is configured such that the light received from a larger region on the banknote 100 can be condensed and the condensed light is output from the single light outputting section 11B.

In this manner, one of the characteristic features of the banknote recognition apparatus 1 according to the present embodiment is that, plural lights are received from plural regions or a light is received from one larger region on the banknote 100 by using the light guide 10 or the light guide 11, the received lights are condensed into one light, and the condensed light is used later to perform a recognition processing on the banknote 100. Because the optical processing unit 3 and the recognition processing unit 4 perform processing using the condensed light, there is no need to provide plural sensors as in the conventional technology. Accordingly, the structure of the device becomes simpler and the manufacturing costs can be reduced as compared to the conventional device. Moreover, although the optical characteristics are measured in plural regions, because the optical characteristics of each of the regions are not used separately, that is, because the condensed light is used, processing can be performed speedily.

Figure 3A:
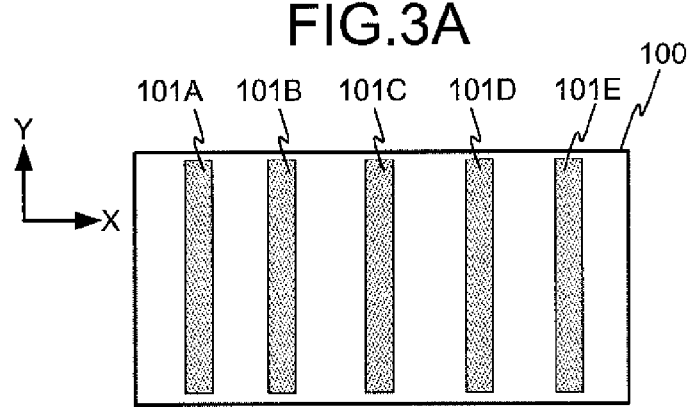
FIGS. 3A to 3D are schematic diagrams for explaining measurement regions where the light guides according to the first embodiment perform measurement.

An example of regions on the banknote 100 where the light guide 10 or the light guide 11 perform measurement are shown in FIGS. 3A to 3D. When the light guide 10 shown in FIG. 2A is used, as shown in FIG. 3A, the light can be received from each of the five independent regions 101A to 101E on the banknote 100, which passes in the Y axis direction below (minus Z axis direction) the light guide 10, at the corresponding light receiving sections 10A to 10E.

Figure 3B:
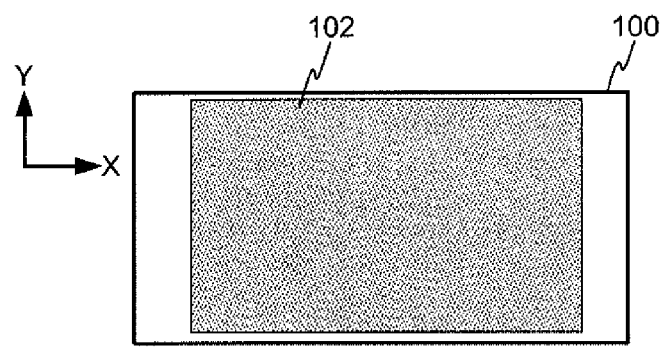
Figure 3C:
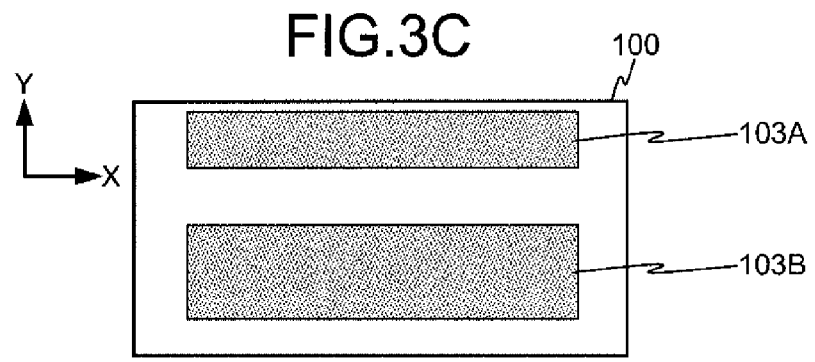

When the light guide 11 shown in FIG. 2B is used, as shown in FIG. 3B, a light can be received from a larger region 102 on the banknote 100, which passes below the light guide 11, at the light receiving section 11A. Moreover, by controlling the timing of emission of the light from the light sources 2, as shown in FIG. 3C, it is possible to receive the light only from partial regions 103A and 103B on the banknote 100, which passes below the light guide 11, in the direction of movement of the banknote 100 (Y axis direction). Even with the light guide 10 shown in FIG. 2A, it is possible to perform the measurement only in a partial region in the Y axis direction.

Other than the technique of using the light guide 10 or the light guide 11 and condensing the light received from the plural regions, it is possible to measure a light separately from the plural regions. Concretely, in case of the light guide 11 shown in FIG. 2B, although the light receiving section 11A is provided on only one surface, as shown in FIG. 1B, because the plural light sources 2 are arranged at separated positions, by controlling the timing of emission of the light from each of the light sources 2, as shown in FIG. 3D, it is possible to make partial regions 104A to 104E on the banknote 100 as the measurement target regions and receive the light separately from those regions.

Figure 3D:
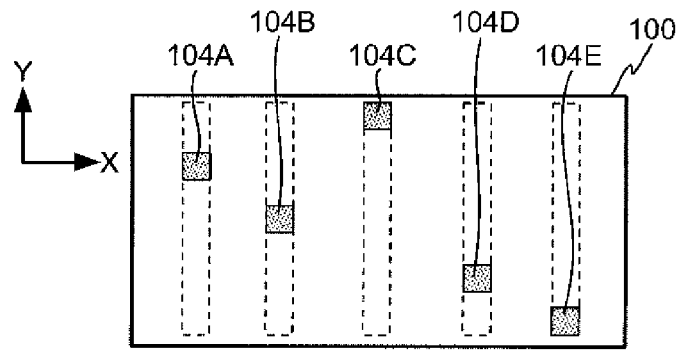

Even when the light guide 10 shown in FIG. 2A is used, as shown in FIG. 3A, by controlling the timing of emission of the light from each of the light sources 2 arranged corresponding to each of the light receiving sections 10A to 10E, as shown in FIG. 3D, it is possible to make the partial regions 104A to 104E, which correspond to each of the light receiving sections 10A to 10E, on the banknote 100 as the measurement target regions and receive the light from each of those regions. In the case of the light guide 10 shown in FIG. 2A, because the measurement target regions are limited to and have a one to one correspondence with the light receiving sections 10A to 10E, the partial regions 104A to 104E can be more accurately determined as the measurement target regions if compared to the light guide 11 shown in FIG. 2B.

It should be noted that, by matching the positions of each of the regions 104A to 104E, shown in FIG. 3D, in the Y axis direction, it is possible to perform measurement of arbitrary selected two, three, or four regions at the same time.

In this manner, by controlling the shapes of the light guides 10 and 11, the ON timing of the light sources 2, or the amount of the light to be emitted from the light sources 2, the position and the region on the banknote 100 from where the light is to be received can be changed. If there should be the banknote 100 as a recognition target that requires detection of the optical characteristics in only one region, then it is possible to handle this banknote 100 by controlling the measurement region of the light guides 10 and 11. By performing measurement only in the partial region in which the optical features is easily obtainable, it is possible to reduce the load on the post-processing of the measurement result and perform the recognition speedily. Moreover, when the measurement region is limited in this manner, by suppressing the effect of other regions on the measurement result, the recognition accuracy of the banknote 100 can be improved.

The light guides 10 and 11 shown respectively in FIGS. 2A and 2B, when seen from the side (X axis direction), as against the front view seen in the same diagrams, have a thin plate-like structure. For example, as against the dimension of several tens of millimeters to hundred millimeters in the length and breadth (X axis direction and Z axis direction) in the front view, the thickness is only about 5 millimeters. However, these dimensions are not limiting. For example, the light guides 10 and 11 can even be made longer than the width (dimension in the X axis direction) of the banknote 100.

The light guides 10 and 11 shown respectively in FIGS. 2A and 2B are simply examples. That is, the shapes of the light guides 10 and 11 can be decided appropriately based on the measurement target regions on the banknote 100 as the recognition target, and a positional relationship between the banknote 100 and the optical processing unit 3. Concretely, for example, the light guides 10 and 11 can have shapes substantially L-shaped form or U-shaped form from the side of the light receiving section toward the light outputting section. Moreover, the number of the light receiving sections is also not limited.

When the light guides 10 and 11 are used, the degree of freedom increases in the arrangement position of the optical processing unit 3 with respect to the position on the receiving light from the banknote 100. Accordingly, the banknote recognition apparatus 1 can be downsized. Moreover, as the light received from the banknote 100 is condensed and used in the light guides 10 and 11, the recognition processing can be performed with sufficient amount of light reaching a single unit of the sensor.

Moreover, the measurement position and the measurement region on the banknote 100 can be changed by changing the shapes of the light guides 10 and 11, or by controlling the arrangement position or the ON timing and the like of the light sources 2, so that the optical characteristics of the light obtained by condensing at the light guides 10 and 11 can be changed. Accordingly, by changing the shapes of the light guides 10 and 11, or by controlling the arrangement position or the ON timing and the like of the light sources 2 in accordance with the optical characteristics of the banknote 100 as the processing target, the banknote 100 can be recognized accurately.

Concretely, for example, for a certain banknote 100, as shown in FIG. 3A, if the optical characteristics used in the denomination recognition are obtained from the regions 101A to 101C, the optical characteristics used in the authenticity recognition are obtained from the regions 101D and 101E, then the measurement region can be suitably selected in accordance with the type of recognition to be performed. In the current example, the optical characteristics required for the denomination recognition and the optical characteristics required for the authenticity recognition can be obtained in one measurement. Moreover, as the measurement can be made only in the required region, the processing can be performed speedily. Furthermore, as the banknote 100 is recognized by obtaining the optical characteristics effective for the recognition processing, the denomination and the authenticity can be recognized accurately.

One of the characteristic features of the light guides 10 and 11 is that the light obtained in plural regions on the banknote 100 can be condensed therein for recognition process.

Figure 9:
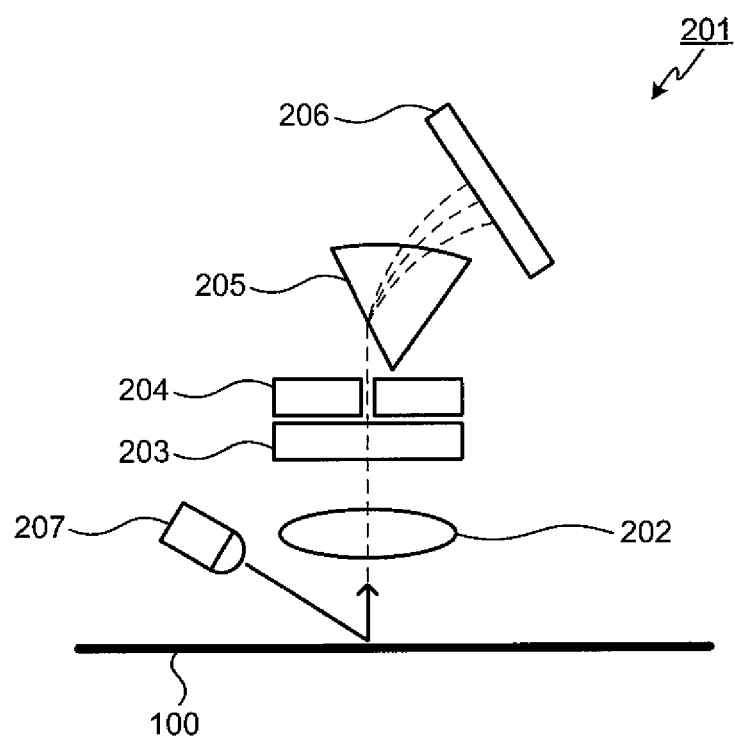
FIG. 9 is a schematic structural diagram of a device that is used for assessing the optical properties of the light guide.

An example of performing a recognition processing by using a banknote recognition apparatus shown in FIG. 9 is explained below. In a banknote recognition apparatus 201, a light is emitted from a light source 207 toward the banknote 100, the light reflected from the banknote 100 is condensed by a condensing lens 202, the light is then converted into a parallel light by a collimate lens 203, the parallel light then passes through a slit provided in a slit member 204, the light is then dispersed by a prism 205, and finally, a reflected light intensity of each wavelength component of the light is measured at a CCD sensor 206. The detailed structure, function, and operation of this conventional banknote recognition apparatus 201 have been disclosed in, for example, International Patent Publication No. 2009/157049.

In the present embodiment, the light guide 10 shown in FIG. 2A is used instead of the condensing lens 202, the collimate lens 203, and the slit member 204. Moreover, the light emitted from the light source 207 on the banknote 100 and then reflected from the banknote 100 is received by the light receiving sections 10A to 10E of the light guide 10. The light guide 10 is arranged so that the light output from the light outputting section 10F enters the CCD sensor 206 in the same manner as the light that comes out from the slit of the slit member 204 enters the CCD sensor 206. Subsequently, the light is dispersed at the prism 205, and the banknote 100 is recognized based on the spectral distribution measured at the CCD sensor 206.

Figure 4A:
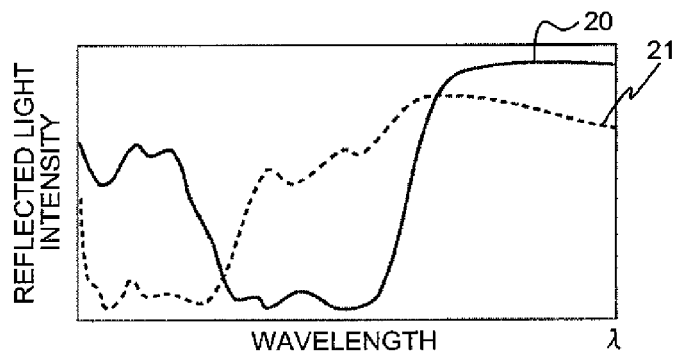
FIGS. 4A to 4D are graphs for explaining that the light guides according to the first embodiment possess optical properties that make it possible for them to recognize a banknote.

Accordingly, in the banknotes 100 that have two different types of denominations, if the measurement is performed at the regions 101A to 101E shown in FIG. 3A, spectral distribution shown in FIG. 4A can be obtained. As seen in FIG. 4A, spectral distributions 20 and 21 of two types of the banknote 100 can be clearly distinguished. That is, the denomination of the banknote 100 can be recognized by using the light guide 10 based on the spectral distributions 20 and 21.

Figure 4B:
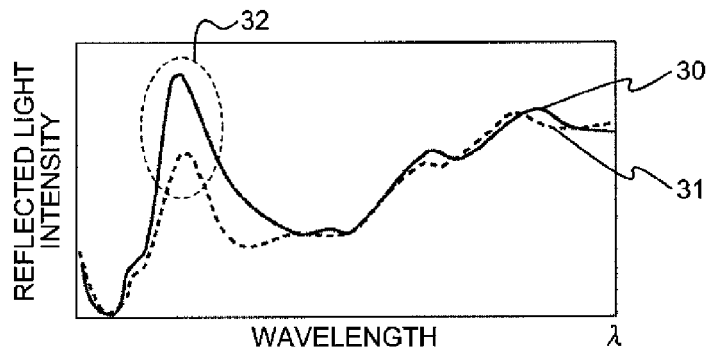

Depending on the denomination of the banknote 100, for example, as shown in FIG. 4B, there can be a situation where two spectral distributions 30 and 31 substantially coincide in a wider wavelength region. Even in this case, the spectral distributions 30 and 31 of the two banknotes 100 can be clearly distinguished in a certain wavelength region 32, so that the denomination of the banknote 100 can be recognized. That is, the banknote recognition becomes possible by simply replacing a part of the optical system of the conventional device with the light guide 10 and 11 according to the present embodiment.

FIGS. 4A and 43 are simply examples. For example, it is possible to recognize the denomination of the banknote 100 in the same manner by using the light guides 10 and 11 shown in FIGS. 2A and 2B by selecting measurement regions as shown in FIGS. 3B to 3D on the banknote 100 and performing measurement in the selected regions. Moreover, it is possible to recognize the authenticity of the banknote 100 by using the light guides 10 and 11. Typically, in recognizing the denomination and the authenticity of the banknote 100, spectrums (20, 21, 30, and 31) shown in FIGS. 4A and 4B obtained from the banknote 100 as the recognition target are, for example, compared with reference data, which are prepared for each denomination and stored previously in a storage device and the like, to make a recognition decision. Because, the decision process is the same as the conventional decision process, detailed explanation thereof has been omitted herefrom.

One of the characteristic features of the present embodiment is that the banknote 100 can be recognized with the light guide 10 or the light guide 11 by effectively using the light of a wide wavelength band. However, there is no limitation on the type of the inspection light. For example, as in the conventional technology, the ultraviolet light or the infrared light having a certain wavelength band can be used. Concretely, the ultraviolet light or the infrared light having the certain wavelength band can be emitted toward the banknote 100 as the inspection light, and, as shown in FIGS. 3A to 3C, spectral analysis can be performed on the reflected light reflected from each of the regions on banknote 100 and condensed with the light guide 10 or the light guide 11. Even in this case, it is possible to recognize the denomination and the authenticity of the banknote 100 by detecting the features of each of the banknote 100 from the result of the spectral analysis in the same manner as in FIGS. 4A and 4B.

Concretely, for example, assuming that a certain security mark has been printed on a partial region 104D shown in the FIG. 3A on the banknote 100 with a fluorescent ink that responds to the ultraviolet light, by emitting the ultraviolet light in this region 104D and performing spectral analysis, presence or absence of the security mark can be determined and the determination result can be used to perform authenticity recognition and the like. Such spectral analysis can be performed for each of the partial regions, or the spectral analysis can be performed continuously in a certain region and the banknote can be recognized based on a variation in the spectrum. For example, assuming that plural security marks are printed with the fluorescent ink in a partial region 101C shown in FIG. 3A, the ultraviolet light is continuously emitted in this partial region 101C, and the banknote is recognized based on the variation in the spectrum of the received reflected light. In any case, the reference data used in the recognition decision is prepared previously, the measured data and the reference data are compared, and the result of this comparison is used to perform recognition of the banknote 100.

According to the present embodiment, it is possible to perform, based on one spectral distribution, recognition of not only any one between the denomination and the authenticity but also both of them simultaneously. Moreover, as shown in FIGS. 3A to 3D, according to the present embodiment, it is possible to set plural measurement regions on the banknote 100. Accordingly, a region that can be used to perform measurement of the optical characteristics that are effective for the recognition of the denomination, and a region that can be used to perform measurement of the optical characteristics that are effective for the recognition of the authenticity can be set, and the recognition of the denomination and the authenticity can be performed simultaneously by generating respective spectral distributions by condensing the respective lights received from these regions by using the light guide 10 or the light guide 11.

The horizontal axis in FIGS. 4A and 4B represents the wavelength and the vertical axis represents the reflected light intensity of each wavelength. It is known that fitness detection of the banknote 100 can be performed from a feature of a spectral waveform of a certain wavelength band of the spectral distribution shown in FIGS. 4A and 4B.

Figure 4C:
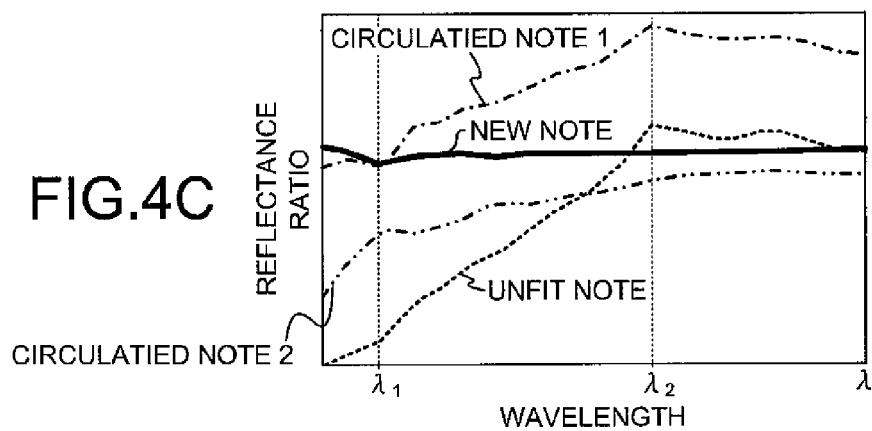

Then, it is explained hereinafter that the fitness detection of the banknote is possible from the measurement result obtained by using the light guides 10 and 11 according to the present embodiment. FIG. 4C represents a case where standardization of the measurement result of each of the banknote is performed by taking the spectral distribution of a new unused note as a reference, and the intensity ratio with respect to this reference note is plotted along the vertical axis and the wavelength is plotted along the horizontal axis. On the other hand, from the result obtained from similar standardization, a tangent line y=ax+b is obtained for the wavelength region defined by wavelengths between λ1 and λ2 as shown in FIG. 4C, and the inclination "a" is plotted along the horizontal axis and the intercept "b" is plotted along the vertical axis to obtain FIG. 4D for plural fit and unfit notes. In this example, the fit notes include new unused notes and notes from circulation.

Figure 4D:
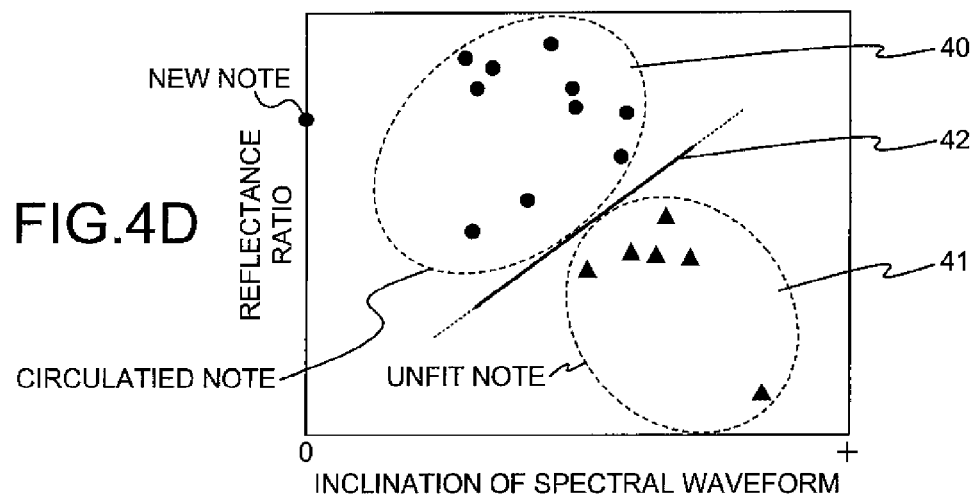

In FIG. 4D, the values obtained from the banknotes 100 that should be recognized as fit notes are shown with solid circles and the values obtained from the banknotes 100 that should be recognized as unfit notes are shown with solid triangles. If a line representing a threshold 42 is set, with this line as a boundary, a distribution 40 of the banknotes 100 that should be recognized as fit notes and a distribution 41 of the banknotes 100 that should be recognized as unfit notes can be separated. That is, the fitness of the banknote 100 can be detected by comparing a feature amount calculated from the spectral distribution obtained by using the light guides 10 and 11 with the threshold.

The feature amount that can be used for the fitness detection is not limited to the inclination of the spectral distribution. For example, reflected light intensities that generates the spectral distribution can be used as the feature amount. Concretely, as the reflected light intensities of the fit notes and the unfit notes are different, by setting a threshold that makes it possible to distinguish between the fit notes and the unfit notes, fitness detection can be performed by comparing the reflected light intensity with the threshold. In this case, there is no limitation on the number of the sensors. Moreover, with respect to the wavelength of the light used for measurement, as long as it is possible to measure the difference in the reflected light intensities arising due to the different fitness, measurement can be performed with only a single wavelength or plural wavelengths. For example, the detection of the fitness of a banknote can be achieved by comparing a threshold with a grand total of all the reflected light intensities obtained with plural wavelengths and measured with a single unit of the sensor, or a grand total of all the reflected light intensities obtained with a single wavelength and measured with plural units of the sensors.

In this manner, in the present embodiment, the recognition of the banknote 100 is performed with a method that is different from that used in the conventional device 201 by using the light guide 10, 11 that has the optical properties that allow recognition of the denomination, the authenticity, and the fitness of the banknote 100. Concretely, interference fringes are generated by the optical processing unit 3 from the light reflected from the surface of the banknote 100 and the generated interference fringes are measured at a CCD sensor 55. Then, the interference fringes are converted into a frequency distribution at the recognition processing unit 4, and the banknote 100 is recognized based on the frequency distribution. These processing performed by the banknote recognition apparatus 1 will be explained in detail below.

First, as shown in FIGS. 1A and 1B, the light emitted from the light sources 2 toward the banknote 100 is reflected from the banknote 100 and the reflected light enters the light guide 10 or the light guide 11. The light that has entered the light guide 10 or the light guide 11 then enters the optical processing unit 3 from the light guide 10 or the light guide 11. The interference fringes are generated in the optical processing unit 3 based on the entered light.

FIG. 5 is a schematic structural diagram of the optical processing unit 3. As shown in FIG. 5, the optical processing unit 3 includes a scattering plate 50 that homogeneously scatters the light that has entered the light guide 10 or the light guide 11 arranged on the left side (minus X axis direction) in this diagram and outputs the scattered light; a first 45-degree polarization plate 51 that receives the non-polarized light wave from the scattering plate 50 and converts it into a 45-degree linear polarized light wave; a Wollaston prism 52 that receives the linear polarized light wave from the 45-degree polarization plate and splits the linear polarized light wave into two orthogonally polarized components, an abnormal light (vertically polarized wave) and a normal light (horizontally polarized wave) having an optical path difference (phase difference), by using birefringence; a second 45-degree polarization plate 53 that aligns the oscillation planes of the two polarized components having the optical path difference, i.e., the abnormal light and the normal light; a lens 54 that forms an image by focusing the two optical components on the CCD sensor 55; and the CCD sensor 55 that measures the distribution of the interference light generated by the two optical components as the interference fringes component.

Figure 6:
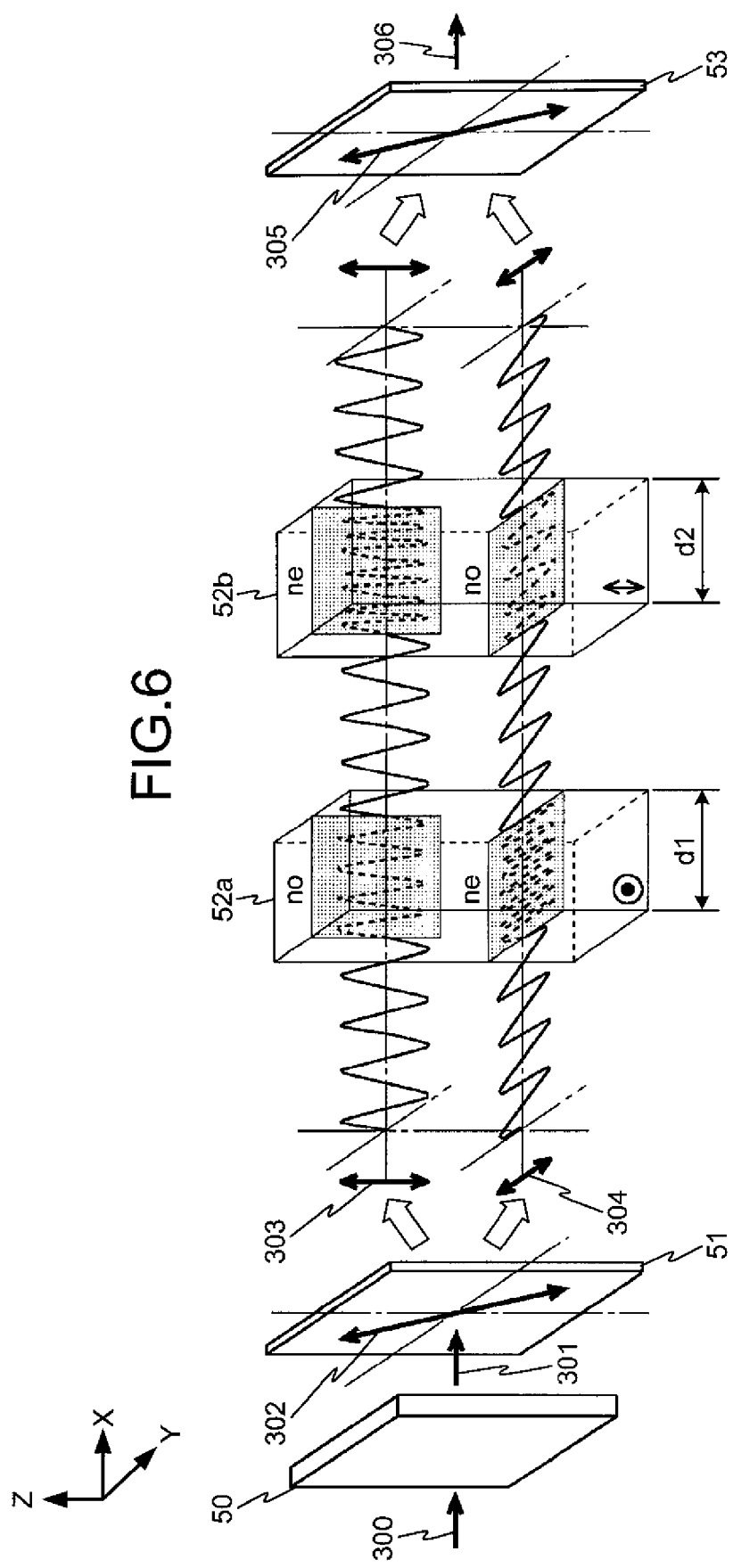
FIG. 6 is a schematic diagram for explaining an optical processing performed by the optical processing unit according to the first embodiment.

The operation of the optical processing unit 3 is explained below in detail. FIG. 6 is a schematic diagram for explaining how the light travels inside the optical processing unit 3.

First, the light 300 that enters the optical processing unit 3 from the light guide 10 or the light guide 11 arranged on the left (minus X axis direction) in FIG. 6 enters the first 45-degree polarization plate 51 after being scattered by the scattering plate 50. The light 300 is converted into a homogeneous light 301 by the scattering plate 50 by removing the effect due to the shape and the like of the light guide 10 or the light guide 11 from the light 300 that is received from the light guide 10 or the light guide 11. The homogeneous light 301 then enters the 45-degree polarization plate 51. In other words, even if the light enters a partial region of the scattering plate 50 from the minus X axis direction, a homogenous light is output along the positive X axis direction of the scattering plate 50 toward the 45-degree polarization plate 51.

Next, the light 301 that enters the 45-degree polarization plate 51, as shown in FIG. 6, is polarized and turned around the X axis to 45 degrees with respect to the Z axis and output as a linear polarized light wave 302. Thus, the non-polarized light 301 that enters the 45-degree polarization plate 51 is output as the 45-degree linear polarized light wave 302.

The Wollaston prism 52 used in the optical processing unit 3 includes, as shown in FIG. 5, a first birefringence member 52a and a second birefringence member 52b having orthogonal crystal orientations with each other. The two birefringence members 52a and 52b are formed from calcite or quartz and the like, and are wedge-shaped when viewed from an orthogonal direction (Y axis direction) to the direction of advance of the light (X axis direction). The birefringence members 52a and 52b adjoin such that, when seen from Y axis direction, they form a rectangle and the surfaces at which they adjoin is a diagonal of this rectangle.

As the Wollaston prism 52 has such a shape, the distances d1 and d2 for which the light travels in the X axis direction within each of these birefringence members 52a and 52b vary depending on the position in the Z axis direction.

That is, when the light enters the Wollaston prism 52 from the lowermost end in the Z axis direction, it travels only through the first birefringence member 52a. As the position of the entry of the light shifts in the positive Z axis direction, the distance d1, which is the distance for which the light travels in the first birefringence member 52a, becomes smaller, while the distance d2, which is the distance for which the light travels in the second birefringence member 52b, becomes longer. Accordingly, when the light enters the Wollaston prism 52 from the topmost end in the Z axis direction, it travels only through the second birefringence member 52b.

As shown in FIG. 6, now assume that a light entering into the Wollaston prism 52 from the positive X axis direction at a certain position in the Z axis direction travels by the distance d1 in the first birefringence member 52a and travels by the distance d2 in the second birefringence member 52b, and a refractive index of the first birefringence member 52a, whose crystal direction is along Y axis direction, is "no" for the abnormal light 303 and "ne" for the normal light 304. In this example, an optical path difference L1 produced between the abnormal light 303 and the normal light 304 due to the difference in the polarization directions will be calculated as $L1=(no-ne)*d1$.

In contrast, the refractive index of the second birefringence member 52b, whose crystal direction is in the Z axis direction, will be "ne" for the abnormal light 303 and "no" for the normal light 304. Accordingly, an optical path difference L2 in this case will be calculated as $L2=(ne-no)*d2$.

In accordance with the Snell's law, the direction of advance of the two orthogonal lights, i.e., the normal light 304 and the abnormal light 303, become inclined by few degrees at the boundary between the birefringence members 52a and 52b. Accordingly, strictly speaking, the optical path length within the second birefringence member 52b is little different from d2. Concretely, the abnormal light 303 advances in a direction that is inclined by 0.5 degree toward the positive Z axis direction from the X axis around the Y axis. For example, when the second birefringence member 52b is made of quartz, and when d2=5 millimeters, the real optical path length becomes 5.0000192 millimeters. In this manner, d2 varies depending on the reflectance and the like of the birefringence members 52a and 52b, however, it can be neglected without harm because the variation amount is very small.

Accordingly, after the light has traveled through both the birefringence members 52a and 52b, an optical path difference L between the abnormal light 303 and the normal light 304 can be calculated as $L=L1+L2=(no-ne)*(d1-d2)$. As shown in FIG. 5, as the value of (d1−d2) varies depending on the position of light entry in the Z axis direction of the Wollaston prism 52, the optical path difference L also varies depending on the position of light entry in the Z axis direction of the Wollaston prism 52.

In this manner, as the optical path difference L between the abnormal light 303 and the normal light 304 varies depending on the position of light entry in the Z axis direction, when these two lights 303 and 304 are caused to interfere, the interference fringes that have a gradation in the Z axis direction are generated.

In view of this, the oscillating surfaces of the two polarized components of the abnormal light 303 and the normal light 304, in which an optical path difference has been produced because of traveling through the birefringence members 52a and 52b, are aligned by using the second 95-degree polarization plate 53 to cause them to interfere. Accordingly, a light 306 that comes out of the 45-degree polarization plate 53 forms interference fringes in the Z axis direction.

Figure 7:
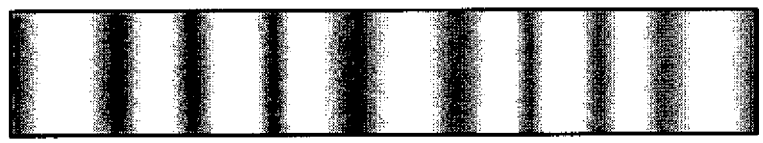
FIG. 7 is a schematic diagram of an example of interference fringes generated by the optical processing unit according to the first embodiment.

The lens 54, as shown in FIG. 5, forms an image by focusing thus obtained two optical components on the CCD sensor 55 in the optical processing unit 3. As a result, the interference fringes as seen in FIG. 7 are measured by the CCD sensor 55.

In this manner, the interference fringes that represent the optical characteristics of the banknote 100 can be formed with the optical processing unit 3. Because the light entering the optical processing unit 3 through the light guide 10 or the light guide 11 is transformed into a different light depending on the optical characteristics of the banknote 100, the interference fringes measured by the CCD sensor 55 also vary depending on the banknote 100. Accordingly, the banknote 100 can be recognized based on the features appearing in the interference fringes.

The recognition processing unit 4 shown in FIGS. 1A and 1B performs Fourier conversion on the interference fringes measured by the CCD sensor 55. That is, by performing the Fourier conversion on the interference fringes shown in FIG. 7, the recognition processing unit 4 obtains a frequency distribution shown in FIG. 8. Because this frequency distribution has been obtained first by converting the light received from the banknote 100 into the interference fringes at the optical processing unit 3, and then by performing the Fourier conversion on the interference fringes at the recognition processing unit 4, different frequency distributions are obtained depending on the optical characteristics of the banknote 100. Accordingly, the banknote 100 can be recognized based on the position and the value (magnitude) of the peak appearing in the frequency distribution.

Figure 8:
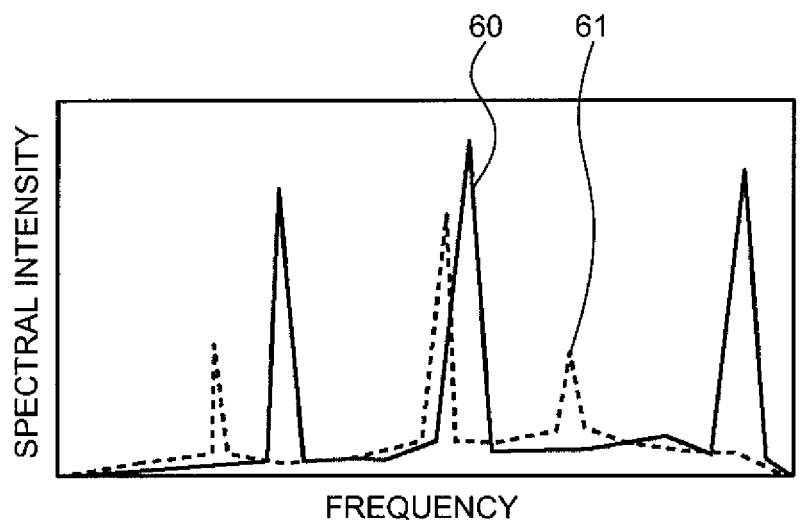
FIG. 8 is a schematic diagram of an example of a frequency distribution obtained by Fourier conversion of the interference fringes.

Concretely, for example, as shown in FIG. 8, in frequency distributions 60 and 61 obtained by measurement from two different types of banknotes 100 in denominations by using the banknote recognition apparatus 1, frequencies at which the peaks appear and heights of the peaks are different. The recognition processing unit 4 compares the frequency distributions 60 and 61 obtained in this manner and performs recognition of the banknotes 100 based on the features such as the frequencies at which the peaks appear and the heights of the peaks. As explained with reference to FIG. 4, therefore, the recognition of the banknotes 100 can be performed by using the difference in the frequency distributions appearing due to the difference in the denominations, the fitness, the authenticity, and the like. FIG. 8 is just an example, and it is possible that the spectrum may not have a peak, and the spectrum may have a waveform as shown in FIG. 4A or FIG. 4B. Even in these cases, however, it is possible to recognize the banknotes 100 based on the difference in the spectrums.

If the optical characteristics of the banknote 100 as the processing targets are measured previously by using the banknote recognition apparatus 1, and the measurement result are stored in a storage device such as a memory and the like as the reference data, a type of various banknotes 100 can be recognized by comparing the measured data with reference data. Moreover, it is possible to perform recognition of the banknotes 100 by setting different thresholds that make it possible to differentiate the types of the denominations, the fitness, the authenticity, and the like. Because the recognition processing for recognizing the banknotes 100 is the same as that used in the conventional technology, the details thereof have been omitted herefrom.

Examples as shown in FIGS. 1A and 1B in which the reflected lights reflected from the banknote 100 after being irradiated with the lights from the light sources 2 are received in the light receiving sections of the light guide 10 or the light guide 11; however, the present embodiment is not limited to this structure. For example, it is possible to employ a structure in which a light is emitted on the banknote 100 from the opposite side (minus Z axis direction) of the banknote 100 with respect to the light guide 10 or the light guide 11 and use a transmitted light. Whether to use the reflected light or the transmitted light, or use both the reflected light and the transmitted light, can be appropriately determined based on the features of the banknotes 100 so that the optical characteristics that make the banknote 100 to be recognized easily and accurately. Similarly, the shapes of the light guides 10 and 11 and measurement positions and measurement regions of the light on the banknote 100 can also be appropriately decided so that the banknotes 100 as the recognition targets can be recognized easily and accurately.

An example has been explained above in which the light-guiding plate of the light guide 10 or the light guide 11 is made of resin; however, the present embodiment is not limited to this structure. For example, an optical fiber and the like can be used as the light-guiding member.

As explained above, according to the present invention, the optical characteristics of the surface of the banknote 100 are measured by using the light guide 10 or the light guide 11. As a result, higher flexibility can be achieved in selecting the position of arrangement of the optical processing unit 3 with respect to the banknote 100, and the banknote recognition apparatus 1 can be downsized. By downsizing the banknote recognition apparatus 1, its manufacturing costs can be reduced.

Moreover, because the light guide 10 or the light guide 11 has been used, various things become possible. For example, measurement of the optical characteristics of the banknotes 100 can be performed in one larger region, or the measurement can be performed in smaller partial regions. Moreover, it is possible to set the measurement positions and the measurement regions depending on the optical features of the banknotes 100 to make the optical characteristics easy to detect. Accordingly, it is possible to accurately measure the optical characteristics of the banknotes 100 and accurately recognize the banknotes 100. Moreover, depending on the regions set on the banknote, for example, regions set for measuring the optical characteristics for denominating, or regions set for measuring the optical characteristics for authentication, and the like, it is possible to recognize either the denomination or the authenticity in one recognition processing, or it is possible to recognize both the denomination and the authenticity in one recognition processing.

The light guide 10 or the light guide 11 can be manufactured inexpensively and easily by using a transparent resin material and the like. This makes it possible to prepare various types of light guides corresponding to the types of the banknotes 100, and to select an appropriate light guide depending on the banknote 100 as the processing target. Accordingly, the optical characteristics of each of the banknotes 100 can be accurately measured and the banknotes 100 can be recognized accurately.

Moreover, because the light obtained from plural smaller regions or one larger region on the banknote 100 is used in the recognition processing after condensing in the light guide 10 or the light guide 11, a light having a higher intensity becomes available for use as compared to a situation where the light is not condensed. Accordingly, the measurement precision of the optical characteristics of the banknotes 100, and the recognition precision of the banknotes 100 can be improved. Moreover, by using the light containing all the wavelength bands instead of using the light containing only a partial wavelength region of the obtained light, the banknote recognition can be performed by effectively using the light. Moreover, because the intensity of the light to be measured is strong, as compared to a situation where the light to be measured is weak, measurement time can be shortened. Accordingly, the total processing time required for the recognition can be shortened.

Moreover, the interference fringes converted from the light obtained from the banknote 100 are used in the optical processing unit 3, then, a light having a higher intensity can be obtained in certain regions by an interference effect as compared to the light that was obtained from the banknote 100. Accordingly, because the optical characteristics are enhanced, the measurement precision of the optical characteristics of the banknotes 100, and the recognition precision of the banknotes 100 are improved.

Moreover, because the processing is executed using the light until before the measurement by the CCD sensor 55, i.e., until the interference fringes are generated, the processing can be performed faster as compared to a case where an image is captured or a case where an image processing is executed on a captured image.

Second Embodiment

An example has been explained as the first embodiment where a single flat plate-shaped light-guiding plate (light-guiding member) was used as the light guide 10 or the light guide 11. In contrast, an example will be explained as the second embodiment where a combination of plural light-guiding plates is used as the light guide. Even in the present embodiment, as in the first embodiment, the light-guiding plates that function as the light-guiding member are used to guide the light received at the light receiving sections to the light outputting section. When a single light-guiding plate is used, this light-guiding plate is the light guide 10 or the light guide 11, and when plural light-guiding plates are used, one light guide is formed by using these light-guiding plates.

FIGS. 10A and 10B are schematic structural diagrams of the banknote recognition apparatus 1 that uses a light guide 400 according to the present embodiment. As shown in FIG. 10A, the banknote recognition apparatus 1 includes the light source 2 that emits a light toward the banknote 100; the light guide 400 that receives reflected lights from the banknote 100, which was irradiated by the light from the light source 2, at respective light receiving sections 501 to 516, and outputs the received light to the optical processing unit 3 from respective light outputting sections 521 to 524; the optical processing unit 3 that receives the light reflected from the banknote 100 via the light guide 400; and a recognition processing unit 4 that processes information obtained by the optical processing unit 3 by processing the light to recognize the banknote 100. Thus, the light guide 400 according to the present embodiment includes 16 units of the light receiving sections 501 to 516. As shown in FIG. 10B, each of the light receiving sections 501 to 516 receives the light reflected from the banknote 100 and emitted from the light source 2.

The functions and operation of the light source 2, the optical processing unit 3, and the recognition processing unit 4 are the same as that mentioned in the explanation of the first embodiment so that detailed explanation thereof has been omitted herefrom. The light guide 400 that is the characteristic features of the present invention will be explained in detail below.

As shown in FIG. 10A, the light guide 400 includes four pieces of the light-guiding plates 401 to 404. Each of the light-guiding plates 401 to 404 is a flat plate-shaped member made of a transparent resin material, such as acrylic resin. In the light-guiding plate 401, four light receiving sections 501 to 504 are arranged facing the banknote 100 along the X axis direction at the same distance from the banknote 100. The light received by these four light receiving sections 501 to 504 are guided along the X axis direction while undergoing total reflection inside the light-guiding plate 401, and output from the light outputting section 521 toward the optical processing unit 3. Similarly, total reflection takes place inside each of the light-guiding plates 402 to 404. Concretely, in the light-guiding plate 402, the lights received by the light receiving sections 505 to 508 are guided to the light outputting section 522, in the light-guiding plate 903, the light received by the light receiving sections 509 to 512 are guided to the light outputting section 523, and in the light-guiding plate 404, the light received by the light receiving sections 513 to 516 are guided to the light outputting section 524.

As shown in FIG. 10A, in the four light-guiding plates 401 to 404, the positions of the light outputting sections 521 to 524 on the side of the optical processing unit 3 are aligned in the Y axis direction. Moreover, the length in the X axis direction decreases from the light-guiding plates 401 to 402, 402 to 903, and 403 to 404 in order. The length of each of the light-guiding plates 401 to 404 are set such that each of the light receiving sections 501 to 516 are arranged at an equal interval in the X axis direction.

Concretely, the difference in the lengths in the X axis direction of the light-guiding plate 901 and the light-guiding plate 902 is set such that, assuming that the light outputting sections 521 and 522 of the optical processing unit 3 are aligned at the same position in the X axis direction, an interval along the X axis direction between the light receiving section 509 of the light-guiding plate 401 and the light receiving section 505 of the light-guiding plate 402 is equal to an interval in the X axis direction between adjacent light receiving sections (501 to 504 and 505 to 508) in each of the light-guiding plates 401 and 404. The lengths of the light-guiding plate 402 and the light-guiding plate 403, the light-guiding plate 403 and the light-guiding plate 404 in the X axis direction are also set in the same manner. Accordingly, in the light guide 400, 16 light receiving sections 501 to 516 are arranged at an equal interval along the X axis direction. Moreover, although the details of the shape of each of the light-guiding plates 401 to 404 will be given later, these 16 light receiving sections 501 to 516 are arranged in a line along the X axis direction.

Figure 11A:
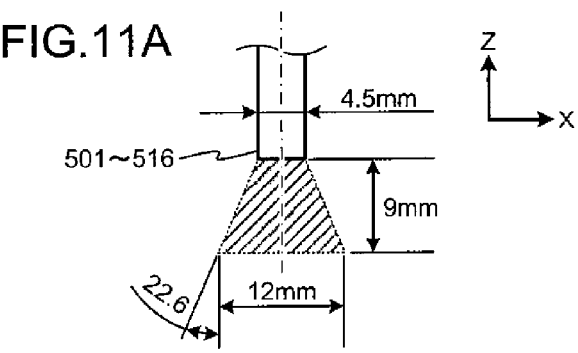
FIGS. 11A to 11D are schematic diagrams for explaining measurement regions where the light guide according to the second embodiment performs measurement.
Figure 11B:
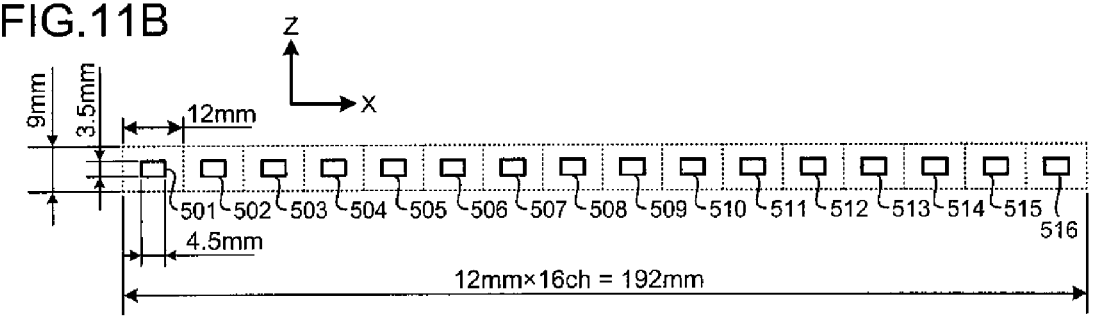

FIGS. 11A to 11D are schematic diagrams for explaining a concrete arrangement of the light receiving sections 501 to 516. FIG. 11A shows a region (hatched region in the diagram) where the optical characteristics of the banknote 100 can be effectively measured with one of the light receiving sections 501 to 516 when seen along the Y axis direction. FIG. 11B shows arrangement positions (solid lines in the diagram) of the 16 light receiving sections 501 to 516 when seen along the Z axis direction, and a region (dashed lines in the diagram) on the banknote 100 of which the optical characteristics can be measured.

As shown in FIG. 11A, a light can be received from a region (hatched region in the diagram) within an aperture angle of 22.6 degrees with the one light receiving section 501 to 516.

Assuming that each of the light receiving sections 501 to 516, which have a rectangular cross-section, has a width of 4.5 millimeters, and the height from the banknote 100 to a receiving surface of the light receiving section is 9 millimeters, then the light can be effectively received from a region that has a width of 12 millimeters in the X axis direction. Accordingly, measurement of the optical characteristics in a continuous band-shaped region on the banknote 100 becomes possible by arranging two adjacent ones among the light receiving sections 501 to 516 such that their central positions are separated at distance not more than 12 millimeters in the X axis direction.

Moreover, when a width in the Y axis direction of the light receiving sections 501 to 516 is set to 3.5 millimeters, similarly, the region from where the light can be received effectively with the height of 9 millimeters and the aperture angle of 22.6 degrees has a width of 11 millimeters in the Y axis direction; however, the region that is measurable in the Y axis direction is subjected to limitation of a casing in which the light guide 400 is housed. Concretely, the light guide 400 housed inside the casing can receive the light only from a region defined by a window for measurement made in the casing. For example, when the casing inside which the light guide 400 is housed has the window for measurement having a width of 9 millimeters in the Y axis direction, then a width of the region that is measurable in the Y axis direction is limited to 9 millimeters.

That is, assuming that the light receiving sections 501 to 516 have rectangular receiving surfaces (solid lines in the diagram) of dimensions of 3.5 millimeters by 4.5 millimeters and they are arranged facing the banknote 100 at a height of 9 millimeters from the banknote 100, then, as shown in FIG. 11B, a rectangular region (dashed lines in the diagram) having dimensions of 9 millimeters by 12 millimeters can be taken as an effective measurement region for one receiving surface (solid lines in the diagram). When the light receiving sections 501 to 516 are arranged at an equal interval in a line along the X axis direction such that the distance between the adjacent light receiving sections is 12 millimeters, taking one light receiving section as one channel, the optical characteristics can be effectively measured for 16 channels in a continuous band-shaped region having a width of 192 millimeters. Accordingly, as long as the width in the X axis direction of the banknote 100 is not more than 192 millimeters, the optical characteristics can be measured from the entire surface of the banknote 100 by passing the banknote 100 below the light guide 400 in the Y axis direction.

In the example shown in FIG. 11B, an arrangement position of each of the light receiving sections 501 to 516 is set such that the respective measurement regions defined by the aperture angle 22.6 degrees at the adjacent light receiving sections 501 to 516 just abut each other in the X axis direction. However, the arrangement positions can be set such that the measurement regions partially overlap each other as long as the entire surface of the banknote 100 can be measured. Moreover, FIG. 11B shows an example in which the light is emitted from the light source 2 simultaneously in plural regions corresponding to plural channels. However, for example, it is allowable to perform the measurement by emitting the light on certain regions on the banknote 100 per certain number of channels such as one channel or two channels. In this case, a partition plate is used to measure accurately in the target regions.

Figure 11C:
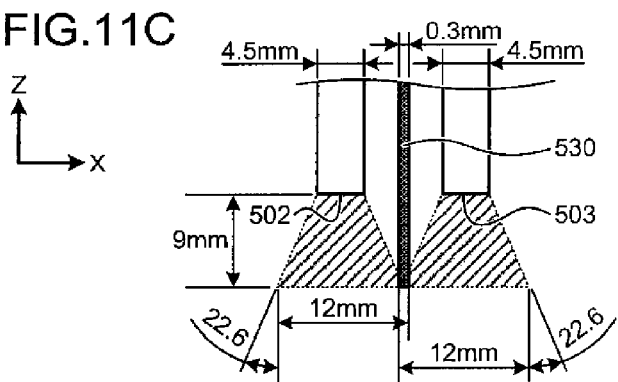
Figure 11D:
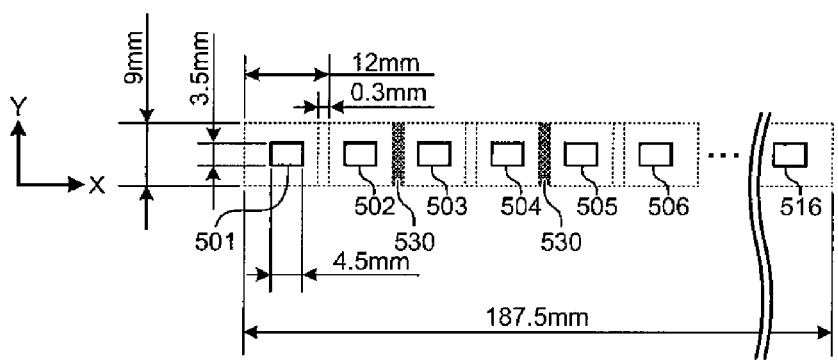
Figure 20A:
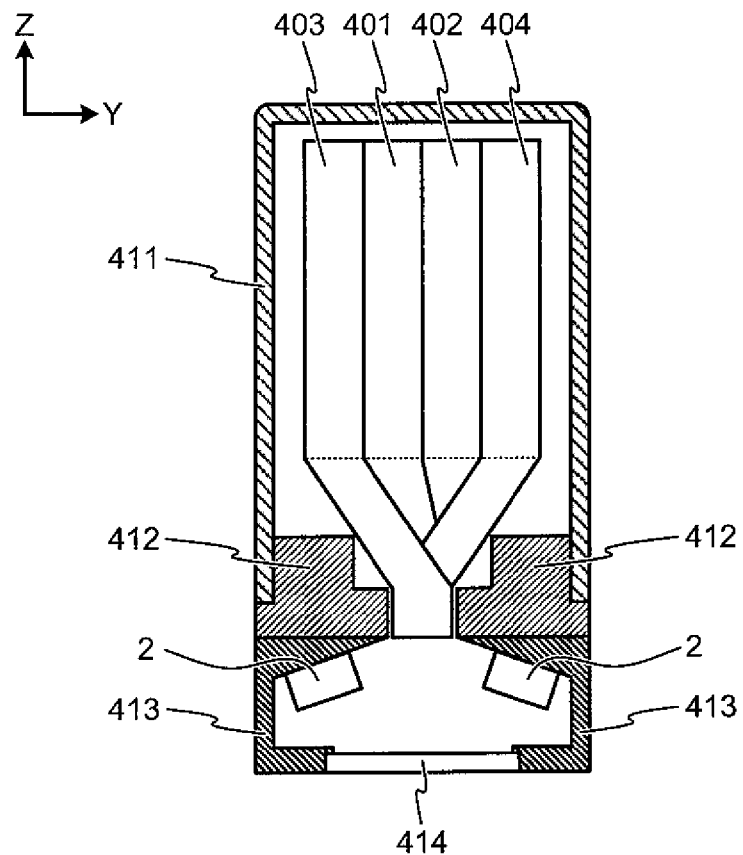
FIGS. 20A and 20B are schematic diagrams showing a cross-section and an outer appearance of a light source unit included in the light guide according to the second embodiment.
Figure 20B:
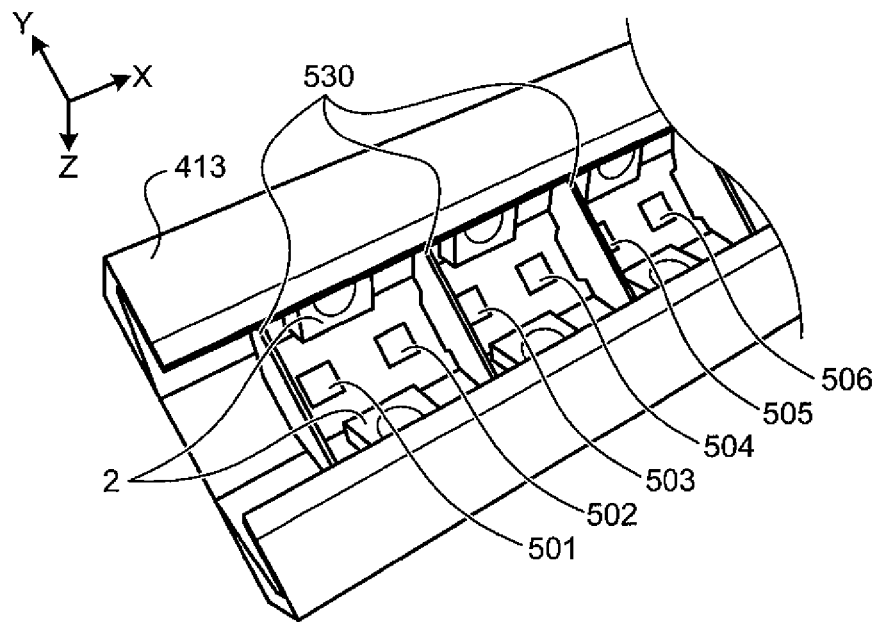

Concretely, for example, as shown in FIG. 11C, a partition plate 530 is arranged between the two light receiving sections 502 and 503. Accordingly, it is possible that the light emitted from the light source 2 corresponding to the light receiving section 502 emits only in the region on the banknote 100 that corresponds to the light receiving section 502, and the light reflected from the banknote 100 from being received at the adjacent light does not come into the receiving section 503. Now assume a case where the 16 channels of the light receiving sections 501 to 516 are grouped into 8 channel-groups when 2 channels are combined into 1 channel-group as shown in FIG. 11D, every two units of the light receiving sections 501 to 516 are separated by the partition plate 530. When using such partition plates 530, as shown in FIG. 20B, the light sources 2 are arranged in each of the compartments partitioned by these partition plates 530. As shown in FIG. 11C, when the light receiving sections 501 to 516 are arranged such that their respective measurement regions overlap by 0.3 millimeter in the X axis direction, then it is possible to measure the optical characteristics in a region having a width of 187.5 millimeters for the 8 channels.

Figure 12:
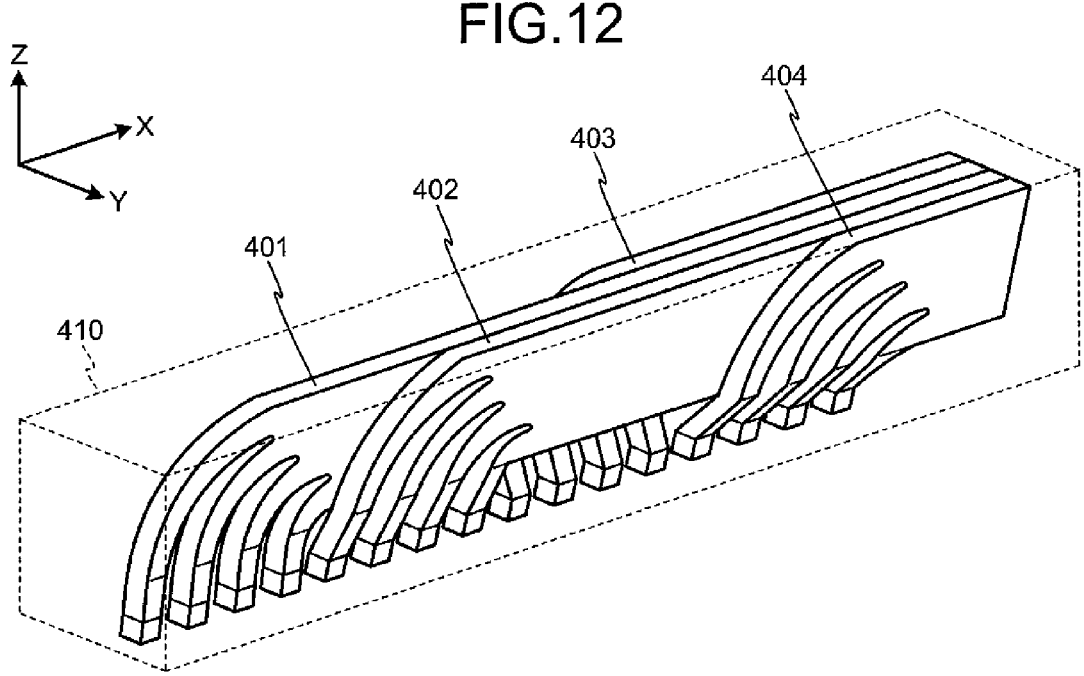
FIG. 12 is a perspective diagram of an outer appearance of the light guide according to the second embodiment.

Next, an explanation will be given about the four light-guiding plates 401 to 404 that constitute the light guide 400. FIG. 12 is a perspective diagram of the light guide 400 that includes the four light-guiding plates 401 to 404. Each of the light-guiding plates 401 to 409 is positioned and fixed within a casing 410 (defined by dashed lines in the diagram).

Although the four pieces of the light-guiding plates 401 to 404 are arranged adjacent to each other along the Y axis direction, the length of each of the light-guiding plates 401 to 404 in the X axis direction is different and adjusted such that the light receiving sections 501 to 516 are arranged at an equal interval along the X axis direction. Moreover, each of the light-guiding plates 401 to 404, in order to arrange the light receiving sections 501 to 516 adjacent to each other in a line along the Y axis direction, are branched into four in a portion from the side of the optical processing unit 3 toward their tips (minus X axis direction), and in a portion after being branched, have a bend in a portion before reaching the light receiving sections 501 to 516.

FIG. 13 is a diagram for explaining the shape of the bend in each of the light-guiding plates 401 to 404 when seen from the minus X axis direction. A cross-section of a base member 412 and a cover member 411 that constitute the casing 410 is also shown in this diagram. An opening that is slightly larger than each of the light receiving sections 501 to 516 is formed in the base member 412 at a position corresponding to each of the light receiving sections 501 to 516. Accordingly, only the light receiving sections 501 to 516 are exposed to the outside from a bottom surface of the casing 910. The positions of the light-guiding plates 401 to 404 are fixed inside the casing 410; however, how the light-guiding plates 901 to 404 are fixed will be explained later.

The shapes of the bends in the light-guiding plate 401 and the light-guiding plate 402, when seen from the minus X axis direction, exhibit symmetry with respect to the Z axis. Similarly, the shapes of the bends in the light-guiding plate 403 and the light-guiding plate 404, which are located on both outer sides, exhibit symmetry with respect to the Z axis. Concretely, the four pieces of the light-guiding plates 401 to 404 are used by being arranged in the manner shown in FIG. 14.

An output efficiency, which represents a ratio of the light that is output from the light outputting sections 521 to 524 with respect to the light received at the light receiving sections 501 to 516, drops as distances between the light receiving sections 501 to 516 and the light outputting sections 521 to 524 increase. Moreover, the more the angle of the bend becomes, the more the total reflectance drops, accordingly the output efficiency also drops. Therefore, the light-guiding plates 401 and 402 are arranged on the inward side so that the bend angles of these two light-guiding plates 401 and 402, for which the light receiving sections 501 to 508 are far away from the light outputting sections 521 to 524, become smaller than the bend angles of the other two light-guiding plates 403 and 404. Concretely, the arrangement position of each of the light-guiding plates 401 to 404 are set such that the larger the decay is due to the distance from the point where the light is received to the point from where the light is output, the smaller the decay will be due to the bend angle.

FIGS. 15A and 15B are schematic diagrams for explaining the shapes of the light-guiding plates 401 to 404. The shape of each of the light-guiding plates 401 to 404 is optically designed such that the light received at each of the light receiving sections 501 to 516 is guided to each of the light outputting sections 521 to 524 while undergoing total reflections inside the light-guiding plates 401 to 404 but without leaking outside of the light-guiding plates 401 to 404. In a portion after being branched and before reaching the light receiving sections 501 to 516, all the light-guiding plates 401 to 404 have the common shape when seen from the Y axis direction. Accordingly, a side shape of only the light-guiding plate 401 is shown in FIGS. 15A and 15B as an example. In order to guide the light received at the light receiving sections 501 to 504, from the light receiving sections 501 to 504 that have the receiving surfaces being orthogonal to the Z axis to the light outputting section 521 that has the receiving surface being orthogonal to the X axis, the side shape in a region where the light-guiding plate 401 is branched into four are made arc-shaped. The extents of the arc-shaped portions are shown with dashed arrows in FIG. 15A.

The radii of curvature R1 to R5 of the arc-shaped portions shown FIG. 15A satisfy a relation R1>R2>R3>R4>R5. Preferably, the arc-shaped portions that lead to each of the light receiving sections 501 to 503 overlap with the adjacent light receiving sections 502 to 504 when they are shifted in the X axis direction. Concretely, for example, it is desirable that an arc-shaped portion of the light receiving section 504 having a radius of curvature R4' of an outer portion and an arc-shaped portion of the light receiving section 503 having the radius of curvature R4 of an inner portion have an overlap when a parallel shift is performed in the X axis direction. Similarly, it is desirable that an outer arc of the light receiving section 503 and an inner arc of the light receiving section 502, and an outer arc of the light receiving section 502 and an inner arc of the light receiving section 501 exhibit an overlapping relation when a parallel shift is performed in the X axis direction.

In the example shown in FIG. 15A, when, for example, the light-guiding plate 401 is such that it satisfies R2'=R2, R3'=R3, and R4'=R4, it is possible that the arc-shaped portions exhibit an overlapping relation when the parallel shift is performed in the X axis direction. The shape at this time, as shown in FIG. 15B, matches with the side-shape when the shift is performed in the X axis direction by different amounts as shown by empty arrows in the diagram, when the four parts that have an overlapping relation with the corresponding arc-shaped portions are arranged at an equal interval with the position of each of the light receiving sections 501 to 504 shifted in the X axis direction.

The arc-shaped portion can be formed, for example, by grinding with a tool having a diameter Ht, or by subjecting the light-guiding plate 401 to a cutting process with a tool such as an end mill having the diameter Ht. However, when forming the arc-shaped portion, only a difference that is equal to the diameter Ht is admissible between the radii of curvature of the corresponding arcs. Concretely, when Ht=0.5 millimeter, then it is admissible that R4=R4'+Ht, R3=R3'+Ht, and R2=R2'+Ht. Moreover, when a width of each of the light receiving sections 501 to 504 in the X axis direction is assumed to be W1, the relation between the radii of curvature can be expressed as R1=R2+W1, R2'=R3'=R4+W1, and R4'=R5+W1.

Moreover, in order to guide the light to the light outputting section 521 while causing total reflections inside the light-guiding plate 401, the radii of curvature are set based on a width of each of the light receiving sections 501 to 504 in the X axis direction. Concretely, when the width of each of the light receiving sections 501 to 504 in the X axis direction is W1, the output efficiency drops significantly if the radius of curvature of the outer arc of the side arc shape is smaller than three times of W1. Accordingly, it is desirable that the radius of curvature of the outer arc is not less than three time of W1. That is, it is desirable that the value of the radius of curvature R4', which is the radius of curvature of the outer arc of the smallest side arc shape, be R4'>3×W1. However, in order to downsize the light guide 400, it is permissible that, giving consideration to the output efficiency, R4' be 2.5 time of W1.

In view of the above discussion, concretely, in FIG. 15A, when W1=4.5 millimeters and the diameter Ht of the tool used to form the light-guiding plate 401 is 0.5 millimeter, then R4' is set to 12 millimeters (>4.5×2.5) and R5 is set to 7.5 millimeters (=R4'−W1). Accordingly, R4 becomes 12.5 millimeters (R4'+Ht) and R3' becomes 17 millimeters (=R4+W1). Similarly, R3 becomes 17.5 millimeters, R2' becomes 22 millimeters, R2 becomes 22.5 millimeters, and R1 becomes 27 millimeters. As a result, a compact light guide 400 having a height of less than 30 millimeters can be achieved.

In the arc shape of each of the light-guiding plates 401 to 404 shown on right side in FIG. 15A, for example, assume that D1=3.5 millimeters and D2=3.35 millimeters. Moreover, the light-guiding plates 403 and 404 that are arranged on the outer side, are bent to have a shape where D3=8.75 millimeters, and the light-guiding plates 401 and 402 that are arranged on the inner side, are bent to have a shape where D4=5.15 millimeters. Furthermore, the light-guiding plate 401 to 404 of which height is H1=30 millimeters has a region with a height H2=19.2 millimeters from the top and a region with a height H3=3 millimeters from the bottom and these two regions are parallel to the Z axis. The light-guiding plates 401 to 404 are bent so that these two parallel regions connect each other. The shape of the bend of each of the light-guiding plates 401 to 404 is not limited to those shown in FIGS. 15A and 15B where a cross-section is linearly bent. For example, it is allowable that the cross-section shape is curved.

How the light-guiding plates 401 to 404 having such shapes are fixed inside the casing 410 is explained below. FIGS. 16A to 16C are schematic diagrams for explaining how the light-guiding plates 401 to 404 are fixed inside the casing 410. FIG. 16A is a schematic cross-sectional diagram showing the base member 412 and the cover member 411 included in the casing 410 when seen from the Y axis direction, and the right view corresponds to a situation seen from the positive X axis direction, and the lower view corresponds to a situation seen from the minus Z axis direction. FIGS. 16B and 16C are schematic diagrams that show how the light-guiding plates 401 and 402 are fixed to the upper side, and respectively show a schematic cross-section taken along the positive X axis direction at positions A and B shown in FIG. 16A.

The lower view of FIG. 16A shows how the receiving surfaces of the light receiving sections 501 to 516 are exposed to the outside from openings 601 to 616, which are through-holes, provided in the base member 412. In this manner, when the light-guiding plates 401 to 404 are positioned and fixed inside the casing 410, the light receiving sections 501 to 516 are exposed to the outside from the openings 601 to 616 provided in the base member 412.

Moreover, in the casing 410, which includes the base member 412 and the cover member 411, when the cover member 411 is put on the base member 412 and fixed, a sealing member, or a packing, is arranged in a gap therebetween to achieve a dust preventing structure. Because of this dust preventing structure, undesired rising of temperature and generation of dew condensation can be prevented from occurring inside the casing 410, and dust is prevented from entering into the casing 410. Concretely, as shown in a left-upper view of FIG. 15R, at a front-end side, a gap between the base member 412 and the cover member 411 is sealed with a sealing member 421. Moreover, at a rear-end side, a gap between the base member 412 and the light-guiding plates 401 to 404 on the periphery, and gaps between each of the light-guiding plates 401 to 404 are sealed with a sealing member 422.

Figure 17A:
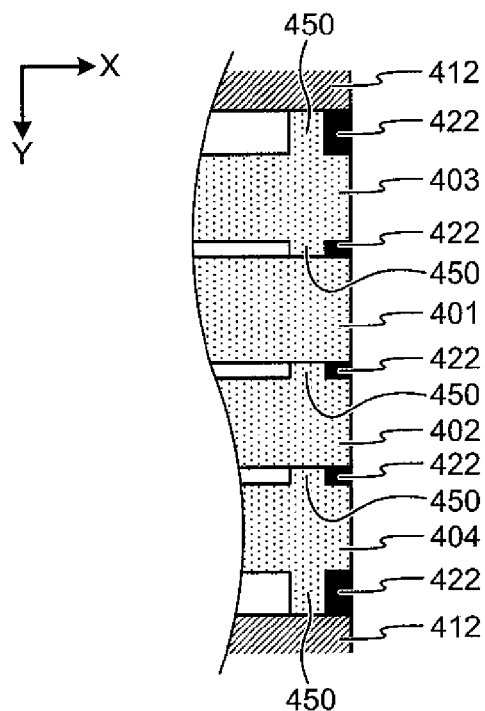
FIGS. 17A and 17B are schematic cross-sectional diagrams for explaining a seal member arranged on a light output side of the light guide according to the second embodiment.
Figure 17B:
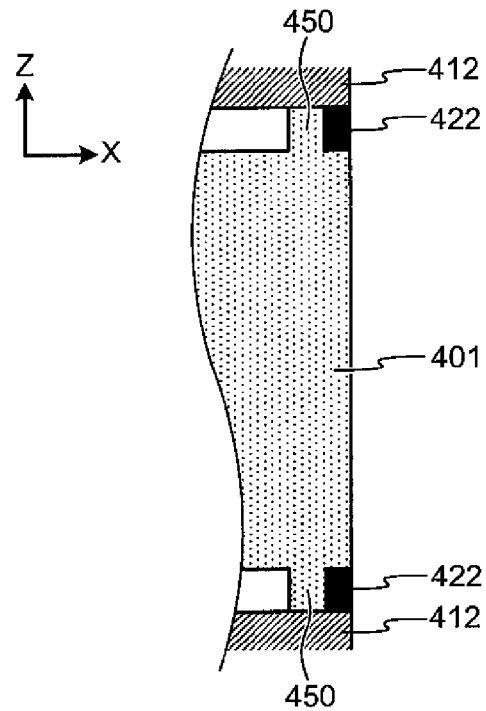

In the light-guiding plates 401 to 404, it is desirable that the light received at the light receiving sections 501 to 516 undergoes total reflection inside the light-guiding plates 401 to 404 without leaking to the outside and output in an effective manner toward the optical processing unit 3 from the light outputting sections 521 to 524. To achieve this, it is desirable that no matter other than air touches the light-guiding plates 401 to 404. As the sealing member 422, it is possible to use a packing and the like made of rubber or resin and previously formed into a predetermined shape, or use a viscous material such as a liquid gasket. When using the viscous material as the sealing member 422, however, care needs to be taken to apply only the minimal quantity to the light-guiding plates 401 to 404. In this regard, a protrusion is arranged on a portion of the light-guiding plates 401 to 404, where the sealing member 422 is applied, to prevent the sealing member 422 application area from enlarging. Concretely, as shown in FIG. 16A and FIGS. 17A and 17B, a protrusion 450 is arranged between the adjacent light-guiding plates 401 to 404, and between the light-guiding plates 401 to 404 and the base member 412. This protrusion 450 prevents more than necessary quantity of the sealing member 422 from intruding and spreading inside.

It is desirable that the light that passes from the light-guiding plates 401 to 404, which are made of a transparent material, toward the sealing member 422 does not leak from the sealing member 422. To achieve this, it is desirable that a material that reflects the light without absorbing it be used as the sealing member 422. For example, when the base member 412 is made of a black resin, by using a white material as the sealing member 422, leakage of the light from the light-guiding plates 401 to 404 to the base member 412 can be prevented. When the base member 412 is made of a material such as a white resin or aluminum that reflects the light, a transparent or semi-transparent material as well as a white material can be used as the sealing member 422.

Subsequently, how the light-guiding plates 401 to 404 are fixed inside the casing 410 is explained. The shape of each of the light-guiding plates 401 to 404 is optically designed such that the light received at the light receiving sections 501 to 516 is guided toward the light outputting sections 521 to 524 while undergoing total reflection inside the light-guiding plates 401 to 404. In order to keep the output efficiency high, when the received light is guided toward the light outputting sections 521 to 524, it is desirable that, to prevent a leakage of the light outside of the light-guiding plates 401 to 404, the light-guiding plates 401 to 404 do not touch the cover member 411 made of aluminum and the base member 412 made of resin that constitute the casing 410. In the same manner, in order to prevent a leakage of the light from among each of the light-guiding plates 401 to 404, it is desirable that the light-guiding plates 401 to 404 do not touch each other. To achieve this, as shown in FIG. 16A, the light-guiding plates 401 to 404 are positioned and fixed with the minimal contact area by using lower holding members 440 to 443 and upper holding member 430 to 432.

The light-guiding plate 401 is positioned and fixed at a certain position in the Y axis direction by using the lower holding member 440 and the upper holding member 430. A groove is formed in the lower holding member 440, which is arranged on the base member 412, to perform positioning of the light-guiding plate 401. The position of the lower part of the light-guiding plate 401 can be fixed by inserting the light-guiding plate 401 in this groove. Moreover, as shown in FIG. 16B, a fixing member 434 is arranged in the upper holding member 430, which is provided to the cover member 411, to fix a plate spring 433 to a main body. This plate spring 433, which is bent at one part thereof, functions to fix the light-guiding plate 401 by pressing its upper side surface to a surface formed in the main body parallel to the XZ plane.

Figure 18A:
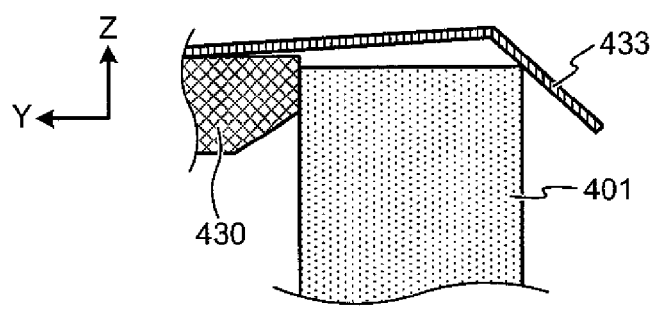
FIGS. 18A and 18B are schematic cross-sectional diagrams for explaining how the light-guiding plate according to the second embodiment is fixed.
Figure 18B:
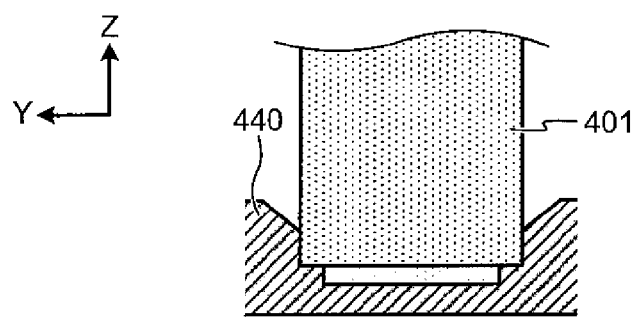

FIGS. 18A and 18B are enlarged views that depict how the light-guiding plate 401 is held by the upper holding member 430 and the lower holding member 440. As shown in FIG. 18A, a main body of the upper holding member 430 has a tapered cross-section. Concretely, as compared to a thickness along the Z axis direction of the main body at a position where the plate spring 433 is fixed, the main body is thinner at a position where it makes a contact with the light-guiding plate 401 so that a contact area with the light-guiding plate 401 gets smaller while positioning the light-guiding plate 401 in the Y axis direction. Moreover, even for the plate spring 433, only a part of a region that is bent in the Z axis direction comes in contact with an upper corner of the light-guiding plate 401. Furthermore, even the shape of the lower holding member 440 is such that, as shown in FIG. 18B, it supports only a lower corner of the light-guiding plate 401 so that a contact area with the light-guiding plate 401 gets smaller, while positioning the light-guiding plate 401 in the Y axis direction and the Z axis direction. The lower holding member 440 is, for example, about 1 millimeter thick in the X axis direction.

When plural plates among the light-guiding plates 401 to 404 are to be held with the upper holding members 431 and 432 and the lower holding members 441 and 443, similarly, they are held such that contact areas therebetween are small. For example, as shown in FIG. 16C, in the upper holding member 431 of the cover member 411, two pieces of the light-guiding plates 401 and 402 are fixed by pressing the upper side surface of the light-guiding plates 401 to a surface formed in the main body parallel to the XZ plane with the plate spring 435 that is fixed with the fixing member 436. In the same manner as shown in FIG. 18B, two pieces of the light-guiding plates 401 and 402 are held and fixed from below in the groove that is formed in the lower holding member 441 on the base member 412.

Figure 19A:
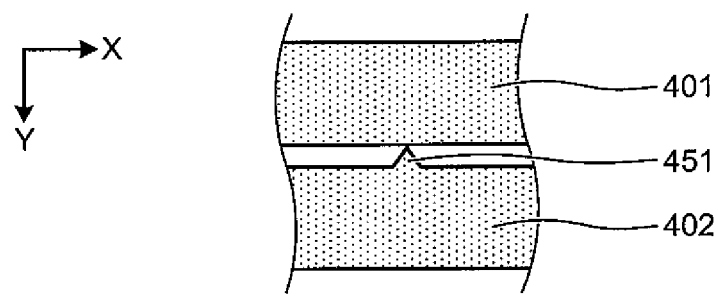
FIGS. 19A and 19B are schematic cross-sectional diagrams for explaining how a gap is secured between the light-guiding plates according to the second embodiment.
Figure 19B:
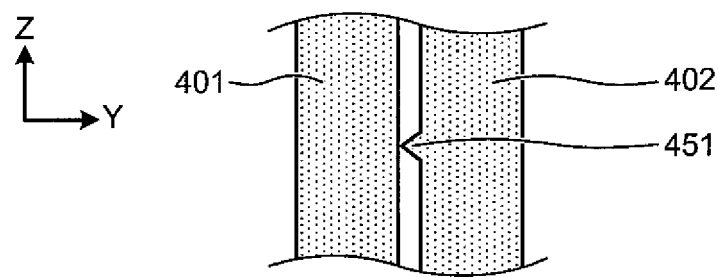

The light-guiding plates 401 to 404 are fixed in such a manner that their side surfaces do not make a contact with each other in a wide area. Concretely, as shown in FIGS. 19A and 19B, for example, a minute protrusion 451 is provided on a side surface of the light-guiding plate 402. Because of this protrusion 451, a gap is secured between the side surfaces of the light-guiding plates 401 and 402 so that these surfaces do not come in contact with each other. The protrusion 451 is conical, and a gap of, for example, about 0.1 millimeter is secured between the light-guiding plates 401 to 404 with the protrusion 451. The protrusion 451 is provided at such a position that the effect on the output efficiency can be reduced to the minimal by taking into account the optical path through which the light received at the light receiving sections 501 to 516 is guided to the light outputting sections 521 to 524 while undergoing total reflection inside the light-guiding plates 401 to 404.

By suppressing the contact area with the light-guiding plates 401 to 404 to the minimal when fixing the light-guiding plates 401 to 404, it is possible to prevent a leakage of the light to the outside on the way when the light is guided from the light receiving sections 501 to 516 to the light outputting sections 521 to 524. Similarly, because each of the light-guiding plates 401 to 404 are fixed such that their side surfaces do not make a contact with each other in a wide area, instead, a certain gap is secured between their side surfaces, it is possible to prevent a leakage of the light from between the light-guiding plates 401 to 404. Moreover, because each of the light-guiding plates 401 to 404 are positioned, as shown in the lower view of FIG. 16A, each of the light receiving sections 501 to 516 can be arranged at an equal interval in a line along the X axis direction while exposing them from the openings 601 to 616 provided in the base member 412. Furthermore, the light-guiding plates 401 to 404 are covered with the base member 412 and the cover member 411, and the gaps is sealed with the sealing members 421 and 422. Accordingly, dust and the like is prevented from entering into the casing 410 and adhering to the light-guiding plates 401 to 404.

A unit that is shown in FIG. 10A that houses the light source 2 is attached below the casing 410 that houses the light-guiding plates 401 to 404. FIG. 20A is a schematic cross-sectional diagram of a situation where a casing 413 that houses the light source 2 as the light source unit is attached below the base member 412. Side surfaces of the casing 413 are made of opaque aluminum or resin, and the window for measurement 414 that faces toward the banknote 100 is made of transparent acrylic resin. When, as shown in FIGS. 11C and 11D, the light receiving sections 501 to 516 are separated from each other with the partition plates 530, as shown in FIG. 20B, the partition plates 530 are arranged. For example, when the light receiving sections are used by grouping two units of the light receiving sections into one group (one channel), then the partition plate 530 is arranged between every group. As a result, one partition plate 530 is arranged between the light receiving sections 501 and 502 and another partition plate 530 is arranged between the light receiving sections 503 and 504. Accordingly, the light receiving sections which constitute one group and the light source 2 that is used for measurement at the light receiving sections are located inside one compartment partitioned by the partition plates 530. Accordingly, the light of the light source 2 corresponding to the light receiving sections 501 and 502 can be emitted on those regions on the banknote 100 that correspond to the light receiving sections 501 and 502, and the light reflected from those regions can be received at the light receiving sections 501 and 502 and prevented from being received at the light receiving sections 503 and 504 in the adjacent compartment.

The light output from the light outputting sections 521 to 524 of the light-guiding plates 401 to 404 is subjected to filtering in the optical processing unit 3 or the recognition processing unit 4 shown in FIG. 10A, so that a light of only desired wavelength band is used. By adjusting the wavelength bands to be subjected to filtering, depending on the type of the banknote 100, a light of only desired wavelength band can be used.

Moreover, when a light of a certain wavelength band is always filtered out regardless of the type of the banknote 100, then the configuration is not limited to the one in which the light output from the light outputting sections 521 to 524 is subjected to the filtering. For example, filtering out can be performed even by using the light-guiding plates 401 to 404.

Figure 21:
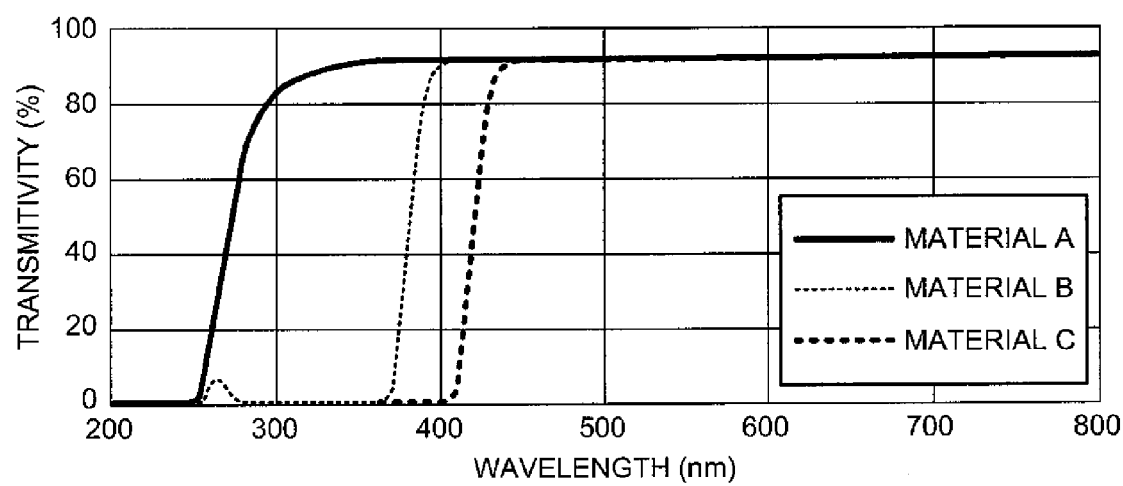
FIG. 21 is a schematic diagram showing spectral transmission characteristics of the material of the light-guiding plates according to the second embodiment

Concretely, a light of a certain wavelength band can be filtered out by selecting the material of the light-guiding plates 401 to 404. For example, three types of transparent resin material A to C respectively having spectral transmission characteristics shown in FIG. 21 can be prepared. When the light-guiding plates 401 to 404 are formed of the selected material B or material C, lights having wavelengths lower than 350 nanometers can be filtered out with those light-guiding plates 401 to 404. Alternatively, for example, when the light-guiding plates 401 to 404 are formed of the selected material C, lights having wavelengths lower than 400 nanometers can be filtered out with those light-guiding plates 401 to 404.

As explained above, according to the present invention, the optical characteristics of the entire surface of the banknote 100 can be effectively measured by combining plural pieces of the light-guiding plates 401 to 404 and using as the light guide 400.

Moreover, because each of the light-guiding plates 401 to 404 are optically designed such that the light received at the light receiving sections 501 to 516 is guided to the light outputting sections 521 to 524 while undergoing total reflection inside the light-guiding plates 401 to 404, the optical characteristics of the banknote 100 can be effectively measured while realizing a high output efficiency.

Moreover, because a portion of each of the light-guiding plates 401 to 404 that leads the light from the light receiving sections 501 to 516 to the light outputting sections 521 to 524 is formed in the arc-shaped portion and this arc-shaped portion is bent on the way in a direction of thickness, each of the light receiving sections 501 to 516 can be aligned in a line at an equal interval to measure the optical characteristics of the banknote 100. In this case, each of the light-guiding plates 401 to 404 are arranged such that, the bend angles of the light-guiding plates 401 and 402, on which are arranged the light receiving sections 501 to 508 for which the distance from the light outputting sections 521 to 522 is longer, is smaller than the bend angles of the light-guiding plates 403 and 404, on which are arranged the light receiving sections 509 to 516 for which the distance from the light outputting sections 523 to 524 is shorter. Accordingly, the decay amount of the light in each of the light-guiding plates 401 to 404 can be made substantially the same.

Moreover, the contact area between each of the light-guiding plates 401 to 404 and the upper holding members 430 to 432 and lower holding members 440 to 442 that fix each of light-guiding plates 401 to 404 is made small. Accordingly, the leakage of the light from each of the light-guiding plates 401 to 404 to the outside via the contacting portions can be suppressed to the minimal. Moreover, as the casing 410 that houses each of the light-guiding plates 401 to 404 has the dust-proof structure in which the gaps are sealed with the sealing members 421 and 422, a drop in the output efficiency can be prevented; because, dust and water is prevented from entering into the casing 410 and adhering to the surface of the light-guiding plates 401 to 404.

Moreover, the material of the light-guiding plates 401 to 404 can be selected according to the wavelength band of the light that is to be used as the measurement target so as to filter out the light of the certain wavelength band by using each of the light-guiding plates 401 to 404. For example, when the visible light is detected by emitting an ultraviolet light from the light source 2, lights of unwanted wavelength bands can be filtered out by employing each of the light-guiding plates 401 to 404 as a filter before the light reaches the COD sensor 55. By doing so, the S/N ratio (signal to noise ratio) can be improved.

INDUSTRIAL APPLICABILITY

As explained above, the present invention is a useful technology for effectively measuring the optical characteristics of a paper sheet by using a light guide that is made of plural light-guiding plates in order to recognize a denomination and the like of the paper sheet by using the measurement result.

EXPLANATIONS OF LETTERS OR NUMERALS

1 Banknote recognition apparatus
2 Light source
3 Optical processing unit
4 Recognition processing unit
10, 11, 400 Light guide
10A to 10E, 11A, 501 to 516 Light receiving section
10F, 11B, 521 to 524 Light outputting section
50 Scattering plate
51 First 45-degree polarization plate
52 Wollaston prism
52a First birefringence member
52b Second birefringence member
53 Second 45-degree polarization plate
54 Lens
55 CCD sensor
100 Banknote
401 to 404 Light-guiding plate
410, 413 Casing
411 Cover member
412 Base member
414 Window for measurement
421, 422 Sealing member
430 to 432 Upper holding member
433, 435 Plate spring
440 to 443 Lower holding member
450, 451 Protrusion
530 Partition plate
601 to 616 Opening

The invention claimed is:

1. A paper sheet recognition apparatus that recognizes a paper sheet based on optical characteristics of the paper sheet, the paper sheet recognition apparatus comprising:
   at least one light source that emits a light toward the paper sheet;
   a light-guiding member that includes a plurality of light receiving sections and a light outputting section, the plurality of light receiving sections receiving any of reflected lights or transmitted lights from plural regions on the paper sheet irradiated with the light from the light source, condenses and guides the received lights to the light outputting section;
   an optical processing unit that generates spectral distribution from a light output from the light-guiding member; and
   a recognition processing unit that recognizes the paper sheet based on a feature of the spectral distribution generated by the optical processing unit
   wherein the optical processing unit generates the interference fringes from a light output from the light-outputting section of the light guiding member, and the recognition processing unit recognizes the paper sheet based on a feature of the interference fringes generated by the optical processing unit.

2. The paper sheet recognition apparatus according to claim 1, wherein the feature recognized by the recognition processing unit is at least one of the type of paper sheet and the authenticity of the paper sheet.

3. The paper sheet recognition apparatus according to claim 1, further comprising a light source control unit that controls the light source, wherein the plural light sources are arranged corresponding to plural of regions on the paper sheet, and the light-guiding member receives any of the reflected lights or the transmitted lights from the regions irradiated with the light from the light sources under the control of the light source control unit.

4. The paper sheet recognition apparatus according to claim 1, wherein the optical processing unit includes a first polarization plate that receives the light output from the light-guiding member and converts the received light to a linear polarized light;

a prism that receives the linear polarized light converted by the first polarization plate and outputs an abnormal light and a normal light having mutual phase difference depending on the receiving position of the linear polarized light; and a second polarization plate that receives the abnormal light and the normal light output from the prism and converts the abnormal light and the normal light to a linear polarized light, and the interference fringes are generated by the linear polarized light output from the second polarization plate.

5. The paper sheet recognition apparatus according to claim 4, wherein the prism is a Wollaston prism that includes a wedged-shaped first birefringence material that has different refractive indexes for the abnormal light and the normal light, and a wedged-shaped second birefringence material that has a different crystal axis than that of the first birefringence material.

6. The paper sheet recognition apparatus according to claim 4, wherein the first polarization plate and the second polarization plate convert the received lights to a linear polarized light wave that is inclined by 45 degrees to a vertical direction.

7. The paper sheet recognition apparatus according to claim 1, wherein the recognition processing unit generates a frequency distribution by subjecting the interference fringes generated in the optical processing unit to Fourier conversion and recognizes the paper sheet based on features of the frequency distribution.

8. The paper sheet recognition apparatus according to claim 1 wherein the plurality of light receiving sections each having a light receiving surface that faces toward the paper sheet to receive a light from the surface of the paper sheet; and the light outputting section that outputs the lights received from the light receiving sections in a direction that is different from a direction from which the lights were received, wherein the plurality of light receiving sections are arranged by adjusting their intervals and heights so that two adjacent light receiving sections are arranged away from each other and their measurement regions where lights can be measured effectively are either in contact with each other or with partially overlapped adjacent sections in an arrangement direction, and lights from a continuous region in the arrangement direction on the paper sheet can be received.

9. The paper sheet recognition apparatus according to claim 8, wherein the light-light guiding member further comprising a plurality of light-guiding plates arranged in an array in a direction of thickness, wherein the plurality of light receiving sections are formed by being separated in each of the light-guiding plates.

10. The paper sheet recognition apparatus according to claim 9, wherein the plurality of light-guiding plates have bend portions respectively that are bent in a direction of thickness at a portion that branches into each of light receiving sections such that, when the light-guiding plates are arranged in the direction of thickness, all the light-guiding plates are aligned in a line.

11. The paper sheet recognition apparatus according to claim 10, wherein each of the light-guiding plates is arranged such that, bend angles of the light-guiding plates, in which a distance from the light outputting sections to the light receiving sections is longer, are smaller than bend angles of the light-guiding plates, in which a distance from the light outputting sections to the light receiving sections is shorter.

12. The paper sheet recognition apparatus according to claim 9, wherein the light-guiding plate has an arc-shaped portion, when viewed from a side thereof, having the uniform cross section from the base of the branch to the end in branch areas leading to the plural light receiving sections.

13. The paper sheet recognition apparatus according to claim 12, wherein an external radius of a first arc-shaped portion and an internal radius of an adjacent second arc-shaped portion at outer side are equal.

14. The paper sheet recognition apparatus according to claim 8, wherein the light-light guiding member further comprising a partition plate that blocks out a light and that is arranged between adjacent light receiving sections.

15. The paper sheet recognition apparatus according to claim 8 further comprising a light guide casing that houses the light-guiding member such that only the light receiving sections and the light outputting section are exposed to outside, wherein the light guide casing comprising:

a base member that positions and supports the light-guiding member from below; and a cover member that positions and supports the light-guiding member from above, wherein the base member and the cover member make a contact with the light-guiding member only at a corner portion of the light-guiding member.

16. The paper sheet recognition apparatus according to claim 15, wherein the cover member includes an upper holding member having a main body and a plate spring fixed to the main body, and the upper holding member positions and fixes the light-guiding member by pressing a side surface of the light-guiding member to the main body by the plate spring.

17. The paper sheet recognition apparatus according to claim 8 further comprising a light guide casing that houses the light-guiding member such that only the light receiving sections and the light outputting section are exposed to outside, wherein the light guide casing comprising:

a base member that supports and performs positioning of the light-guiding member from below; and a cover member that supports and performs positioning of the light-guiding member from above, wherein the base member includes a lower holding member that has a groove portion for positioning the light-guiding member, wherein, inner side surfaces of the groove portion that are extending outward contact with lower corners of the guide light-guiding member partially, and are fixed in a state that the bottom of the light-guiding member does not contact with the bottom of the groove portion.

* * * * *